(12) United States Patent
Yoshida et al.

(10) Patent No.: US 6,320,661 B1
(45) Date of Patent: Nov. 20, 2001

(54) METHOD FOR MEASURING TRANSMITTANCE OF OPTICAL MEMBERS FOR ULTRAVIOLENT USE, SYNTHETIC SILICA GLASS, AND PHOTOLITHOGRAPHY APPARATUS USING THE SAME

(75) Inventors: Akiko Yoshida, Kawasaki; Norio Komine, Sagamihara; Hiroki Jinbo, Yokohama, all of (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/538,965

(22) Filed: Mar. 31, 2000

(30) Foreign Application Priority Data

Apr. 1, 1999 (JP) .................................................. 11-095264

(51) Int. Cl.[7] .............................. G01N 21/00; G01J 1/10; C03B 37/075
(52) U.S. Cl. ................... 356/432; 356/243.1; 250/252.1; 65/397; 501/905
(58) Field of Search ................................ 356/432, 433, 356/443, 434, 239.1, 243.1, 243.4; 250/252.1, 339.09, 341.1, 341.5, 341.6; 428/426, 428, 454; 65/397, 413, 17.3, 17.4; 501/54, 53, 11, 905

(56) References Cited

U.S. PATENT DOCUMENTS

| 5,679,125 | 10/1997 | Hiraiwa et al. | 65/397 |
| 5,776,219 * | 7/1998 | Jinbo et al. | 65/31 |
| 6,129,987 * | 10/2000 | Jinbo et al. | 428/426 |
| 6,174,830 * | 1/2001 | Jinbo et al. | 501/54 |

FOREIGN PATENT DOCUMENTS

| 0 483 752 A2 | 5/1992 | (EP) . |
| 7-63680 | 3/1995 | (JP) . |
| 8-271393 | 10/1996 | (JP) . |
| 10-279322 | 10/1998 | (JP) . |
| 11-211613 | 8/1999 | (JP) . |

* cited by examiner

*Primary Examiner*—Hoa Q. Pham
(74) *Attorney, Agent, or Firm*—Morgan, Lewis & Bockius LLP

(57) ABSTRACT

A method is provided for evaluating a transmittance of an optical member for ultraviolet use, which is an object of measurement. The method includes the steps of cleaning the object of measurement, measuring a transmittance of the object of measurement within a predetermined time period from completion of the cleaning during which a rate of decrease in the transmittance of the object of measurement remains substantially constant, and correcting the transmittance measured in the step of measuring to a transmittance at an evaluation time arbitrarily selected within the predetermined time period in accordance with the constant rate of decrease in the transmittance and a time at which the transmittance is measured.

24 Claims, 10 Drawing Sheets

METHOD FOR MEASURING TRANSMITTANCE OF OPTICAL MEMBERS FOR ULTRAVIOLENT USE, SYNTHETIC SILICA GLASS, AND PHOTOLITHOGRAPHY APPARATUS USING THE SAME

This application claims the benefit of Japanese Application No. 11-095264, filed in Japan on Apr. 1, 1999, which is hereby incorporated by reference.

BACKGROUND OF THE INVENTION

1. Field of the Invention

The present invention relates to a method for evaluating the transmittance of photolithographic optical members used in optical systems, such as lenses and mirrors, which are to be used in a specific wavelength region of about 400 nm or less, preferably about 300 nm or less, in photolithographic techniques.

The present invention also relates to a synthetic silica glass member for use in optical systems, such as lenses and mirrors, which are to be used in a photolithographic apparatus in a specific wavelength region of about 400 nm or less, preferably about 300 nm or less, in a photolithographic technique, and to a photolithographic apparatus that is constructed using such optical members.

2. Discussion of the Related Art

Conventionally, an exposure apparatus called "stepper" has been used in photolithographic techniques in which fine patterns of integrated circuits are exposed and transferred onto wafers made of silicon, etc. In the light source used in such steppers, there has been a progressive shortening of the wavelength of the light source from the g-line (436 nm) to the i-line (365 nm), and further to KrF (248.3 nm) and ArF (193.4 nm) excimer lasers as the degree of integration in LSI has increased in recent years. Thus, general purposes-use optical glass cannot be used in illumination systems or projection lenses of such excimer laser steppers, and materials of silica glass or fluorite, etc., which show high transmittances even in the ultraviolet region—e.g., at the wavelengths of excimer lasers, are required.

Furthermore, the optical system mounted in a stepper is constructed from a combination of numerous lenses. Since the transmittance drop in each lens is multiplied by the number of lenses used, it is necessary to minimize the transmittance drop in each lens in order to prevent a drop in the light power on the wafer and a drop in the throughput. For this reason, it is necessary that the silica glass or fluorite used in the illumination systems or projection lenses of excimer laser steppers have a bulk transmittance of 99.8%/cm or greater, and development aiming at an increase in the transmittance of optical elements used in the ultraviolet region has been pursued.

As the wavelengths of exposure light sources have become progressively shorter, it has become technically difficult to measure the bulk transmittance values of optical elements with high accuracy. Accordingly, a technique for the accurate measurement and evaluation of the bulk transmittance values of synthetic silica glass and crystal materials, etc., which have only a very small absorption (bulk absorption coefficient=approximately 0.001/cm), becomes indispensable for achieving a high transmittance in optical materials. Various types of wet and dry cleaning constitute one technique for the precise measurement and evaluation of the bulk transmittance values of optical materials. Especially in the vacuum ultraviolet region, such as the ArF excimer laser wavelength region (193 nm), the effects of contaminants adhering to the surfaces of evaluation samples on the measured value of the transmittance cannot be ignored. Accordingly, in the transmittance evaluation process, it is essential that the samples to be evaluated (evaluation sample) be cleaned prior to the measurement of the transmittance, so that the surface contaminants are removed.

However, after the surfaces of the evaluation samples have been cleaned by various cleaning methods, contamination by organic substances, etc. (re-contamination), proceeds during the time between the completion of cleaning and the measurement/evaluation of the transmittance, even if this time is short. The reason for this is that trace amounts of organic substances are constantly released from the constituent members of the clean room and the holder or transporting jig used to store the samples into the ambient atmosphere that surrounds the evaluation samples following cleaning. Thus, the surfaces of the evaluation samples that have been cleaned by the above-mentioned cleaning method are exposed to these organic substances. In particular, since there is nothing to prevent the re-adhesion of organic matter to the cleaned surfaces immediately after cleaning, re-contamination of the surfaces by organic matter, which is present in the ambient atmosphere, proceeds quickly.

Furthermore, the quantity of organic matter re-adhering to the surfaces of the samples following cleaning depends on the time from the completion of cleaning to the performance of the transmittance measurement. This means that even if the same samples are cleaned under the same conditions, the transmittance will differ if the time from the completion of cleaning to the measurement of the transmittance differs. This is because the amount of adhering organic matter will be different. Accordingly, in cases where the transmittance values of different samples are to be compared, in addition to cleaning the samples under the same conditions, it is necessary to perform the transmittance measurements at a fixed time following the completion of cleaning. However, in order to ensure that the transmittance is always measured at a fixed time from the completion of cleaning, only one sample must be treated in a single cleaning at a time. Accordingly, in cases where there are a plurality of samples, and especially in cases where the cleaning process requires a long processing time as in wet cleaning, etc., the cleaning process is time-consuming and inefficient since the overall evaluation process takes time.

Furthermore, in order to exclude as far as possible the effects of re-contamination of the surfaces, it is necessary that the measurement of the transmittance of the evaluation samples be performed as quickly as possible following the completion of cleaning. For this, a commercially marketed spectrophotometer, which allows measurements to be performed by a simple method, is suitable. However, in the case of such a spectrophotometer, it is necessary to increase the light power used for measurement as much as possible in order to improve the measurement precision, and it has been impossible to achieve sufficient collimation of the measurement light for this purpose at the position of the object of measurement (i.e., the light has an angle of divergence). As a result, the light path of the measurement light (transmitted light) passing through the object of measurement varies by refraction, so that it has been difficult to make an accurate determination of the transmittance.

Another aspect of the conventional photolithography technologies is described next. In general, the optical systems of such steppers are constructed from an illumination optical system, which uniformly illuminates the surface of a reticle with light from a light source, and a projection optical system, which reduces an integrated circuit pattern on the reticle with a reduction ratio of 1/5, for example, and projects this pattern onto the wafer.

As stated above, in the light source used in photolithographic apparatus, there has been a progressive shortening of the wavelength of the light source from the g-line (436 nm) to the i-line (365 nm), and further to KrF (248.3 nm) and ArF (193.4 nm) excimer lasers as the degree of integration of LSI has increased in recent years. In correspondence with this development, there has been a rising demand for photolithographic apparatus that can expose patterns having a finer minimum finished line width. However, in cases where the wavelength of the light source is in the ultraviolet region, and especially in the region of about 250 nm or less, if the lens materials used in the illumination optical system and projection optical system are materials suited for light with a wavelength longer than the i-line, the resultant light transmittance is poor and such materials are inadequate for practical use. Accordingly, materials that can be used are limited to silica glass and some crystalline materials that have a high transmittance.

Where silica glass members are used in the optical system of a photolithography apparatus, an extremely high quality is required in order to expose integrated circuit patterns over a large area at a high resolution. For example, if the diameter of such a member is relatively large, 200 mm or so, for example, it is necessary that the refractive index distribution of the member be in the order of $10^{-6}$ or less. Furthermore, it is also necessary to reduce the amount of birefringence—i.e., the internal distortion of the member—in order to provide a superior uniformity in the refractive index distribution and the higher resolution of the optical system. Accordingly, even among silica glass materials, silica glass members that can be used in photolithographic apparatus, such as excimer laser steppers using ultraviolet light as a light source, are fairly limited.

Furthermore, in the case of silica glass members used in photolithography apparatus, which uses ultraviolet light as a light source, in addition to the above-mentioned conditions, the members need to have a high transmittance (i.e., a small loss coefficient). The reason for this requirement is that a large number of lenses is used to correct for aberration in the illumination optical system and the projection optical system of a photolithographic apparatus, and the light losses of the individual lenses will lead to a significant drop in the transmittance of the apparatus as a whole.

In addition to fused silica glass obtained by melting a powder of natural quartz, silica glass also includes synthetic silica glass obtained by chemical synthesis. Among these types of silica glass, synthetic silica glass contains smaller amounts of metal impurities and has a higher purity. Accordingly, synthetic silica glass is characterized by a high transmittance even with respect to ultraviolet light having a wavelength of about 250 mn or less. Furthermore, because of the manufacturing method used for synthetic silica glass, homogeneous elements with a large diameter can be manufactured.

However, even in the case of synthetic silica glass, when high-output ultraviolet light or excimer laser light is used, an absorption band at 260 nm caused by structural defects known as NBOHC (non-bridging oxygen hole centers, with a structure of $\equiv$Si—O.) and an absorption band at 215 nm caused by structural defects known as E' centers (having a structure of $\equiv$Si.; here, $\equiv$ does not indicate a triple bond, but rather bonding with three oxygen atoms, and the dot indicates an unpaired electron) appear, so that the transmittance in the ultraviolet region significantly degrades. Since the center wavelengths of these absorption bands are close to the wavelengths of KrF excimer lasers and ArF excimer lasers used as the stepper light sources, the transmittance of the optical system drops significantly by such light absorption. In some cases, the absorption band at 215 nm is strongly generated even if the total amount of ultraviolet irradiation is small (i.e., even if the irradiation energy is low or the irradiation time is short). Since this absorption band sometimes also occurs even in the initial stages of excimer laser irradiation, this absorption is called "bulk-absorption shortly after irradiation". For this reason, not all types of synthetic silica glass can be used as lens members in such apparatus; in order to maintain good practical performance of the apparatus, it is necessary to use a synthetic silica glass in which the above-mentioned "bulk-absorption shortly after irradiation" does not occur or is significantly reduced.

In the past, synthetic silica glass has been obtained in which the loss coefficient prior to irradiation with ArF excimer laser light (wavelength: 193.4 nm) is approximately 0.0020 $cm^{-1}$. However, there has been no glass that can maintain such a high transmittance for a long period of time after irradiation with ArF excimer laser light, and no sufficient practical photolithography apparatus using an ArF excimer laser as a light source has existed in the past.

SUMMARY OF THE INVENTION

Accordingly, the present invention is directed to a method for measuring a transmittance of an optical member for ultraviolet use, synthetic silica glass member, and a photolithography apparatus using the same that substantially obviate the problems due to limitations and disadvantages of the related art.

An object of the present invention is to provide a method for measuring the transmittance of an optical member for ultraviolet use, which makes it possible to make an accurate determination of the transmittance without any effects from re-contamination after cleaning, i.e., without any effects of a drop in transmittance, and which allows transmittance measurements to be performed efficiently for a plurality of objects of measurement.

Another object of the present invention is to provide a synthetic silica glass member, which can increase the transmittance of a photolithographic apparatus using an ArF excimer laser as a light source, and which can show a sufficient practical utility.

A further object of the present invention is to provide a photolithographic apparatus using the synthetic silica glass member of the present invention.

Additional features and advantages of the invention will be set forth in the description that follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the present invention provides a method for evaluating a transmittance of an optical member, which is an object of measurement, for ultraviolet use, the method including the steps of cleaning the object of measurement; measuring a transmittance of the object of measurement within a predetermined time period from completion of the cleaning during which a rate of decrease in the transmittance of the object of measurement remains substantially constant;

and correcting the transmittance measured in the step of measuring to a transmittance at an evaluation time arbitrarily selected within the predetermined time period in accordance with the constant rate of decrease in the transmittance and a time at which the transmittance is measured.

In another aspect, the present invention provides a method for manufacturing a silica glass, including the steps of synthesizing a silica glass ingot; heat-treating the silica glass ingot; cutting out a plurality of silica glass pieces from the heat-treated silica glass ingot; evaluating transmittances of the plurality of silica glass pieces, including the steps of cleaning the plurality of silica glass pieces, for each of the plurality of silica glass pieces, measuring a transmittance of the silica glass piece within a predetermined time period from completion of the cleaning during which a rate of decrease in the transmittance of the silica glass piece remains substantially constant, and for each of the plurality of silica glass pieces, correcting the measured transmittance to a transmittance at an evaluation time arbitrarily selected within the predetermined time period in accordance with the constant rate of decrease in the transmittance and a time at which the transmittance is measured; and selecting silica glass pieces, from among the plurality of silica glass pieces, that have a loss coefficient of about 0.0050 cm$^{-1}$ or less as determined from the transmittance evaluated in the step of evaluating.

In another aspect, the present invention provides a synthetic silica glass member to be installed in a photolithography apparatus using light in the wavelength region of about 400 nm or less, wherein a loss coefficient measured at 193.4 nm of the synthetic silica glass member is about 0.0050 cm$^{-1}$ or less after an ArF excimer laser irradiates the synthetic silica glass with 1×10$^4$ pulses at an energy density of 0.1 μJ/cm$^2$·p to 200 mJ/cm$^2$·p.

In another aspect, the present invention provides a photolithography apparatus using light in the wavelength region of about 400 nm or less, the photolithography apparatus including a plurality of optical members optically coupled with each other for processing the light, wherein at least some of the optical members are made of the synthetic silica glass member described above.

In another aspect, the present invention provides a method for evaluating a transmittance of an optical member for ultraviolet use, the method including the steps of cleaning a surface of the optical member; measuring a transmittance of the optical member with respect to ultraviolet light within a predetermined time from completion of the cleaning during which a rate of decrease in transmittance remains substantially constant; and deriving a transmittance of the optical member at an evaluation time arbitrarily selected within the predetermined time period from the transmittance measured in the step of measuring in accordance with the constant rate of decrease in transmittance and a time at which the transmittance is measured in the step of measuring.

In another aspect, the present invention provides a method for a quality control in manufacture of a plurality of synthetic silica glass members, the plurality of synthetic silica glass members being manufactured under substantially similar manufacturing conditions, the method including the steps of cleaning surfaces of the plurality of synthetic silica glass members; measuring the transmittances of the plurality of synthetic silica glass members within a predetermined time period from completion of the cleaning during which a rate of decrease in the transmittance remains substantially constant, at least some of the plurality of synthetic silica glass members being measured at different times; and for each of the plurality of synthetic silica glass members, converting the transmittance measured in the step of measuring to a transmittance at an evaluation time arbitrarily selected within the predetermined time period in accordance with a time at which the transmittance is measured in the step of measuring and the constant rate of decrease, the evaluation time being set to be the same for all of the plurality of synthetic silica glass members, thereby enabling evaluation of the transmittance without effects of different transmittance decreases due to the different times at which the transmittances are measured in the step of measuring.

In a further aspect, the present invention provides a method for selecting synthetic silica glass members that meet a predetermined standard from a plurality of synthetic silica glass members, the method comprising the steps of cleaning surfaces of the plurality of synthetic silica glass members; measuring transmittances of the plurality of synthetic silica glass members within a predetermined time period from completion of the cleaning during which a rate of decrease in the transmittance remains substantially constant, at least some of the plurality of synthetic silica glass members being measured at different measurement times; for each of the plurality of synthetic silica glass members, converting the transmittance measured in the step of measuring to a transmittance at a fixed evaluation time substantially close to the time of the completion of the cleaning in accordance with a time at which the transmittance is measured in the step of measuring and the constant rate of the transmittance decrease, thereby extrapolating an initial transmittance; and selecting among the plurality of silica glass members silica glass members that meet the predetermined standard in accordance with the initial transmittance extrapolated in the step of converting.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Figure 1:
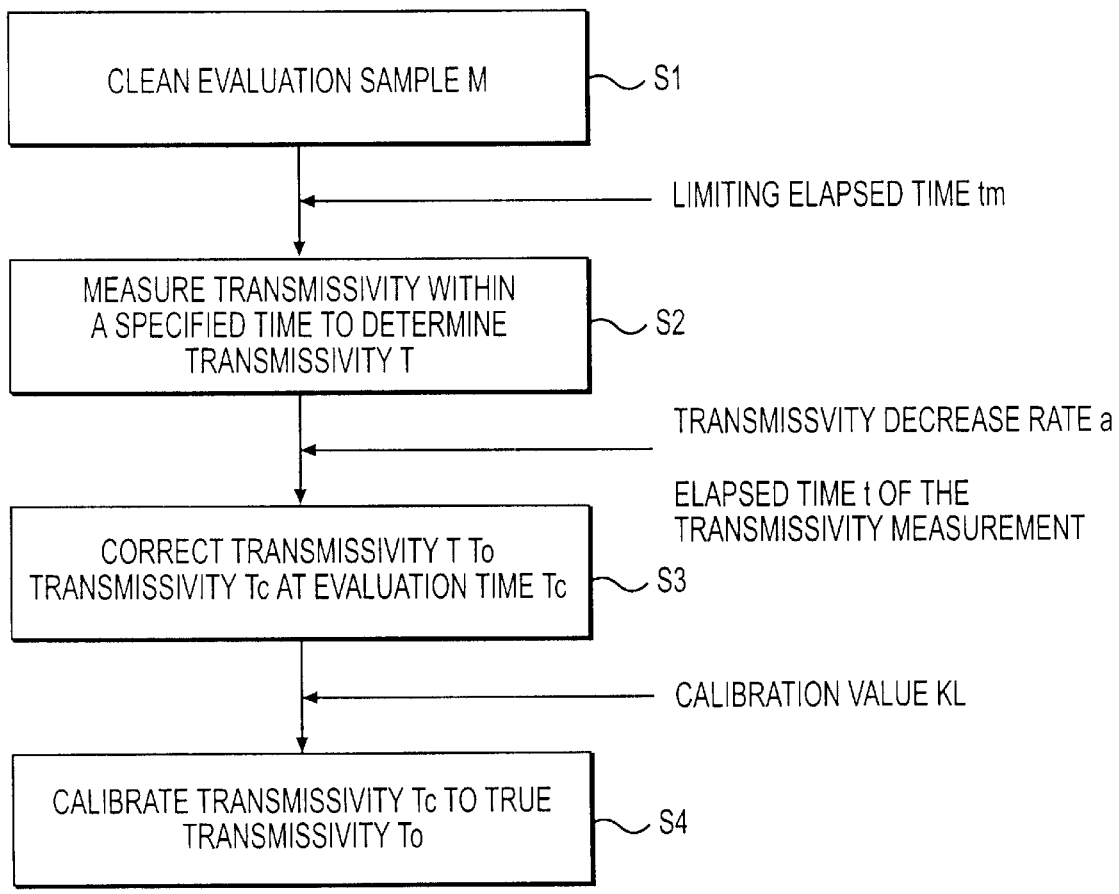
FIG. 1 is a flow chart which illustrates a procedure of a method of the present invention for measuring the transmittance of optical members for ultraviolet use.

Reference will now be made in detail to the preferred embodiments of the present invention, examples of which are illustrated in the accompanying drawings.

Method for Measuring Transmittance

Before describing the preferred embodiments of the method for measuring the transmittance according to the present invention, the inventor's diligent research, which lead to the present invention, is described. In order to achieve the above-mentioned object, the present inventors investigated how the transmittance changes as a result of re-contamination following the completion of cleaning (this refers to the point in time at which the drying process is completed) by examining changes over time in the transmittance of samples for various types of silica glass and fluorite ultraviolet-use optical members that were subjected to various types of wet and dry cleaning (including drying processes). As a result, it was found that the transmittance values of the samples drops with elapsed time from the completion of cleaning; that the rate of this drop is more or less constant up to a certain time; and that the transmittance values depend on the materials and thicknesses of the samples.

Accordingly, if the rate of the drop in transmittance observed during the period in which this rate is constant is defined as the "transmittance decrease rate", and the elapsed time (elapsed time from the completion of cleaning) at which the rate of the drop in transmittance ceases to be constant is defined as the "limiting elapsed time", it can be said that the two parameters of transmittance decrease rate and the limiting elapsed time exist for each sample in accordance with the material and thickness of the sample. Furthermore, if these two parameters are known, then the value of the transmittance measured at an arbitrary elapsed time (elapsed time from the completion of cleaning) within the specified time period during which the rate of the drop in transmittance is constant (i.e., the time period up to the point in time at which the limiting elapsed time has elapsed since the completion of cleaning) can be corrected (converted) to the transmittance at an arbitrarily selected evaluation time within the above-mentioned specified time period. This conversion can be achieved based on the value of the elapsed time (elapsed time from the completion of cleaning) at which the transmittance measurement was actually performed and on the transmittance decrease rate.

Accordingly, a method for measuring the transmittance of an optical member for ultraviolet use according to the present invention includes a first process of cleaning an object of measurement (the optical member for ultraviolet use); a second process of measuring the transmittance of the object of measurement within a specified time period during which the rate of decrease in the transmittance of the object of measurement is constant following the completion of cleaning; and a third process of performing a correction that converts the transmittance, which was obtained by the transmittance measurement at the elapsed time from the completion of cleaning at which the transmittance measurement is performed, into the transmittance at an arbitrarily selected evaluation time within the above-mentioned specified time period, based on the above-mentioned elapsed time and on the value of the above-mentioned decrease rate within the above-mentioned specified time period.

If the above-mentioned evaluation time selected is set to a time close to the completion of cleaning, the transmittance value of ultraviolet optical members determined by this method is the accurate transmittance value that is unaffected by surface re-contamination that proceeds following the completion of cleaning (i.e., unaffected by any drop in transmittance). Accordingly, transmittance measurement may be performed at any elapsed time as long as this elapsed time is within the specified time period during which the rate of the drop in the transmittance of the object of measurement remains constant. Thus, there is a time margin for transmittance measurement. Furthermore, according to this method, where a plurality of objects is to be measured, these objects of measurement are all cleaned at a time, and successive transmittance measurements may be performed thereafter. Accordingly, the time required for transmittance evaluation can be greatly saved.

Since the measurement of transmittance must be performed within the above-mentioned specified time period, a measuring apparatus with a relatively simple construction (e.g., a commercially marketed spectrophotometer) is generally used. Such a measuring apparatus with a relatively simple construction makes it possible to perform transmittance measurements quickly. On the other hand, the problem of instrumental errors arise, which cannot be ignored. Here, the term "instrumental errors" refer to deviations from the true value, which arise due to the fact that light has a divergence angle so that the light path of the measurement light passing through the object of measurement varies by refraction from reference light. Accordingly, in addition to the first through third processes described above, it may be desirable to add a fourth process in which the transmittance at the above-mentioned evaluation time is corrected using a correction value that eliminates the instrumental errors generated in the transmittance measurements. When this is done, quick and accurate transmittance measurements can be performed using a simple measuring apparatus, so that the working efficiency is improved. Here, it goes without saying that if transmittance measurements are performed using a measuring apparatus having sufficiently small instrumental errors, the above-mentioned fourth process may be unnecessary.

Preferred Embodiment

Below, a preferred embodiment of the present invention will be described with reference to the attached figures. Here, a case in which the transmittance of evaluation samples M (thickness=Lo) of ultraviolet-use optical members is measured using a commercially marketed spectrophotometer will be described as an example.

As shown in FIG. 1, the transmittance measurement method according to the present invention proceeds in the order of a first step (S1) in which the evaluation sample M is cleaned (this includes a drying process), a second step (S2) in which a transmittance measurement is performed within a specified time to determine the transmittance T, a third step (S3) in which the transmittance T thus obtained is corrected to a transmittance Tc at the evaluation time tc, and a fourth step (S4) in which the transmittance Tc at the evaluation time is calibrated to a true transmittance To. Here, in order to perform the above-mentioned procedure, it is necessary to determine the transmittance decrease rate "a" and the limiting elapsed time "tm" corresponding to the material and thickness (=Lo) of the evaluation sample, as well as calibration value "$K_L$" of the spectrophotometer beforehand.

Figure 2:
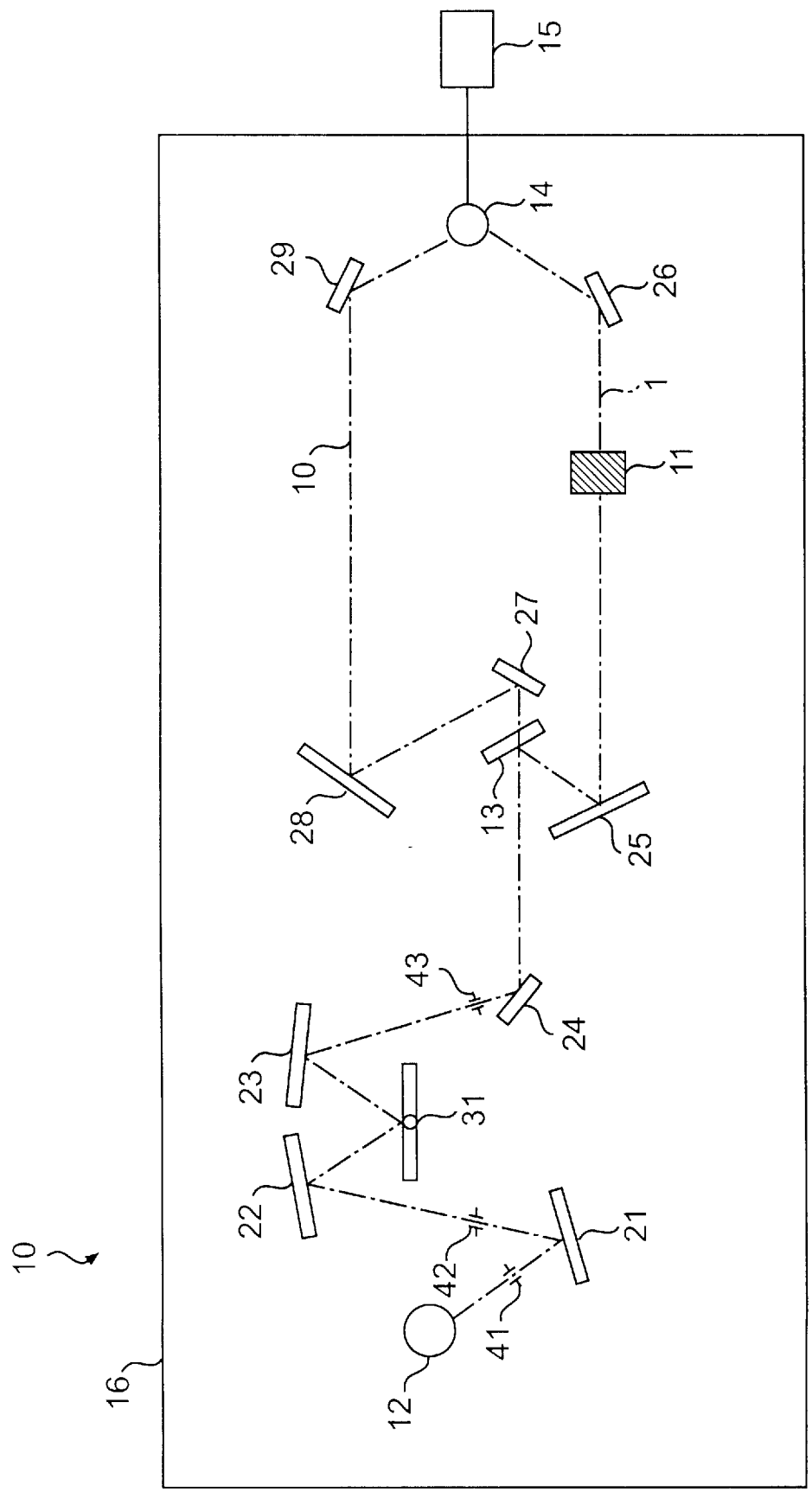
FIG. 2 is a diagram which shows a construction of a spectrophotometer used to measure the transmittance.

First, a spectrophotometer used for this transmittance measurement will be described. FIG. 2 shows an example of the construction of the commercially marketed spectrophotometer. In order to measure the transmittance of an object of measurement 11 using this spectrophotometer 10, the object of measurement 11 is placed between a mirror 25 and a mirror 26, and is illuminated with light (ultraviolet light) from a light source 12. The light from the light source 12 passes through a slit 41 and is incident on a mirror 21. The light reflected by the mirror 21 passes through a slit 42, and is directed onto a diffraction grating 31 via a mirror 22. The first order diffraction light is reflected by a mirror 23, and is directed onto a mirror 24 via a slit 43. The light reflected by the mirror 24 passes through a chopper mirror 13, and is incident on the mirror 25 or a mirror 27. The light (measurement light) reflected by the mirror 25 falls on the object of measurement 11. The light that passes through the object of measurement 11 (the transmitted light) is directed onto a detector 14 via a mirror 26. Meanwhile, the light reflected by the mirror 27 (reference light) is directed onto the detector 14 via mirrors 28 and 29. The transmitted light and the reference light received by the detector 14 are separately processed in a processing device 15 to determine the transmitted light intensity I and the reference light intensity Io. Then, the transmittance of the object of measurement 11 is calculated from the ratio I/Io of these values. Furthermore, the various devices except for the processing device 15 are housed by an air-tight chamber, and this chamber is purged with nitrogen at the time of transmittance measurement.

Next, the procedure used to determine the two parameters of transmittance decrease rate "a" and limiting elapsed time "tm" corresponding to the material and thickness (=Lo) of the evaluation sample M will be described. First, a correction sample, which is formed of the same material and has the same thickness (=Lo) as the evaluation sample M is prepared. Then, the procedure of measuring the transmittance of the sample by means of the spectrophotometer 10 following the cleaning of the sample (including a drying process) is repeated a plurality of times with various different elapsed times—various different times of transmittance measurement (i.e., various times elapsed from the completion of cleaning). The results are plotted on a coordinate plane with the elapsed time on the horizontal axis and the measured transmittance on the vertical axis, thus generating a first plot.

The first plot thus obtained represents changes in the transmittance over time for the correction sample. These plotted points can be fitted by means of a straight line extending from the completion of cleaning to a certain point in time (see FIG. 5, for example). This straight line shows a gradual decrease (i.e., has a negative slope) with an increase in the elapsed time. This slope determines the transmittance decrease rate "a" (%/cm), and a time period, during which the above-mentioned straight line fitting is possible, is read as the limiting elapsed time "tm" (minutes). In this way, the transmittance decrease rate "a" and the limiting elapsed time "tm" are determined for the evaluation sample M.

The reason that both the transmittance decrease rate "a" and limiting elapsed time "tm" obtained using the correction sample can be treated as values for the evaluation sample is that both parameters, i.e., the transmittance decrease rate "a" and the limiting elapsed time "tm", are common where the material and thickness of samples are the same. Accordingly, in cases where the transmittance T at an elapsed time of t (<tm) is determined by performing a transmittance measurement for the evaluation sample M within a predetermined time period during which the transmittance decrease rate is constant (this corresponds to the time period extending from the completion of cleaning to the point in time at which the limiting elapsed time "tm" has passed), this transmittance T can be converted into the transmittance Tc at an arbitrarily selected evaluation time (reference time) tc (<tm) within the above-mentioned predetermined time period by means of the following Equation (1):

$$Tc = T + (t - tc) \times a \quad (1)$$

This transmittance Tc represents the transmittance that would have been obtained if the transmittance were measured at the reference time tc.

Next, a procedure for determining the calibration value $K_L$ of the spectrophotometer 10 will be described. A calibration transmittance measuring apparatus of the type described below is needed in order to calculate this calibration value $K_L$.

Figure 3:
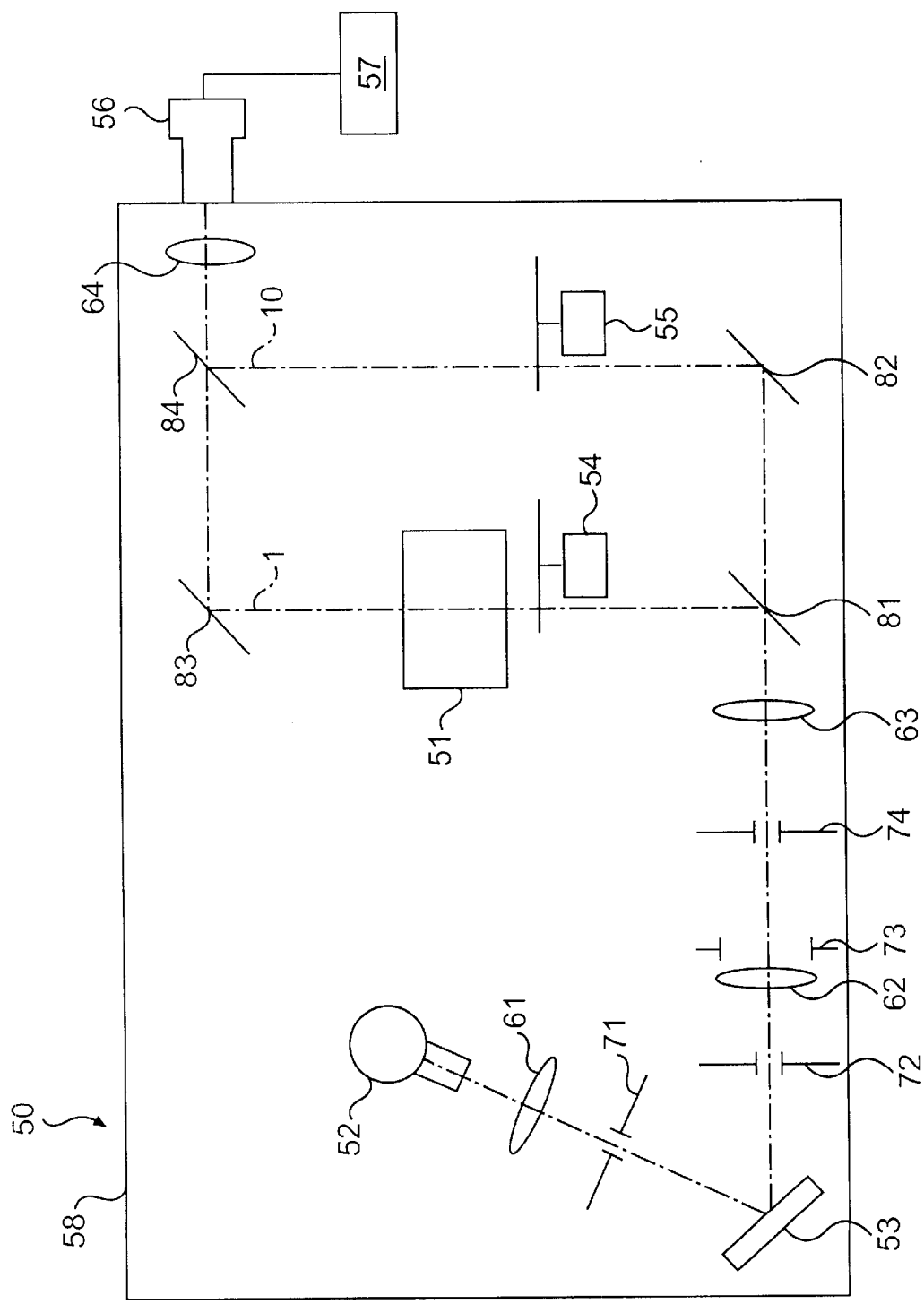
FIG. 3 is a diagram which shows a construction of a calibration transmittance measuring apparatus used to calculate calibration value $K_L$.

FIG. 3 shows an example of the construction of such a calibration transmittance measuring apparatus. In this calibration transmittance measuring apparatus 50, light (ultraviolet light) emitted from a light source 52 is focused by a first focusing lens 61, and is directed onto a diffraction grating 53 via the entry slit 71 of a spectroscope. The light that is reflected and diffracted by this diffraction grating 53 is directed onto a second focusing lens 62 via an exit slit 72 of the spectroscope. At the second focusing lens, the light is again focused, after which a brightness adjustment is performed by means of a diaphragm 73. The light passing through the diaphragm 73 is shaped into a specified shape through a pinhole 74. This light is then converted into parallel light rays through a collimator lens 63, and is directed onto a first half-mirror 81.

The light reflected by the first half-mirror 81 is directed onto an object of measurement 51 via an optical chopper 54 for measurement light use. The transmitted light that passes through the object of measurement 51 is directed onto a detector 56 via a mirror 83, second half-mirror 84 and focusing lens 64. Meanwhile, the reference light that passes through the first half-mirror 81 is directed onto a second half-mirror 84 via a first mirror 82 and an optical chopper 55 for reference light use, and the reference light reflected by the second half-mirror 84 is directed onto the detector 56 via the focusing lens 64. The transmitted light and the reference light received by the detector 56 are separately processed in a processing device 57 to determine the transmitted light intensity I and the reference light intensity Io. Then, the transmittance is determined from the ratio I/Io of the transmittance light intensity I to the reference light intensity Io. Here, the entire apparatus (except for the detector 56 and the processing device 57) is installed in an air-tight manner inside a vacuum chamber 58, so that the atmosphere around the measurement light can be set at a pressure that is close to a vacuum.

Furthermore, the angle of divergence of the measurement light at the position where this light passes through the object of measurement 51 can be adjusted by altering the slit widths of the spectroscope entry slit 71 and spectroscope exit slit 72, by changing the diameter of the pinhole 74, and/or by moving the second focusing lens 62, diaphragm 73, pinhole 74, and collimator lens 63 along the optical axis. This angle of divergence is adjusted to a value of 10 milli-radians (0.57 degrees) or less. This is done in order to reduce variations in the measurement light path caused by refraction in the object of measurement 51. This way, measurement errors that may occur due to irregularities in sensitivity of the light-receiving surface of the detector 56 can be suppressed.

Furthermore, the atmosphere around the light path of the measurement light is adjusted to be close to a vacuum, i.e., to a pressure of $1\times10^{-2}$ Torr (1.33 Pa) or less, or in terms of oxygen partial pressure, to a pressure of $2\times10^{-3}$ Torr (0.27 Pa) or less. This is done in order to reduce the effect of absorption caused by oxygen molecules that exist within a differential between the light path length of the transmitted light and the light path length of the reference light, which in turn results from the fact that the object of measurement 51 has a thickness.

In order to determine the calibration value $K_L$ of the spectrophotometer 10 using the calibration transmittance measuring apparatus 50 constructed as described above, a plurality of calibration samples, which are made of the same material as the correction sample (i.e., the same material as the evaluation sample M), and which have respectively different thicknesses, are first prepared. Furthermore, one of these calibration samples is given the same thickness as the correction sample (i.e., the same thickness Lo as the evaluation sample M; thus, the above-mentioned correction sample itself may also be used). Next, after the calibration samples have been cleaned, the transmittance values T1 of these samples are measured using the calibration transmittance measuring apparatus 50 before the limiting elapsed time "tm" has passed (i.e., within the above-mentioned predetermined time period). Here, the transmittance measurement is performed in the order of the cleaning and the transmittance measurement, one sample at a time, for the respective calibration samples, and the respective measurements are performed such that the elapsed time at the time of transmittance measurement (i.e., the time elapsed from the completion of cleaning) is the same for all of the samples. The reason for adopting such a procedure is that it is difficult in most cases to complete the transmittance measurements for all of the calibration samples before the limiting elapsed time "tm" has passed (so that correction using Equation (1) is not adequate). From the respective transmittance values T1 thus obtained, the losses of the respective calibration samples are determined using Equation (2) shown below.

$$\text{Loss}=-LN(T1/Tth) \qquad (2)$$

Figure 4:
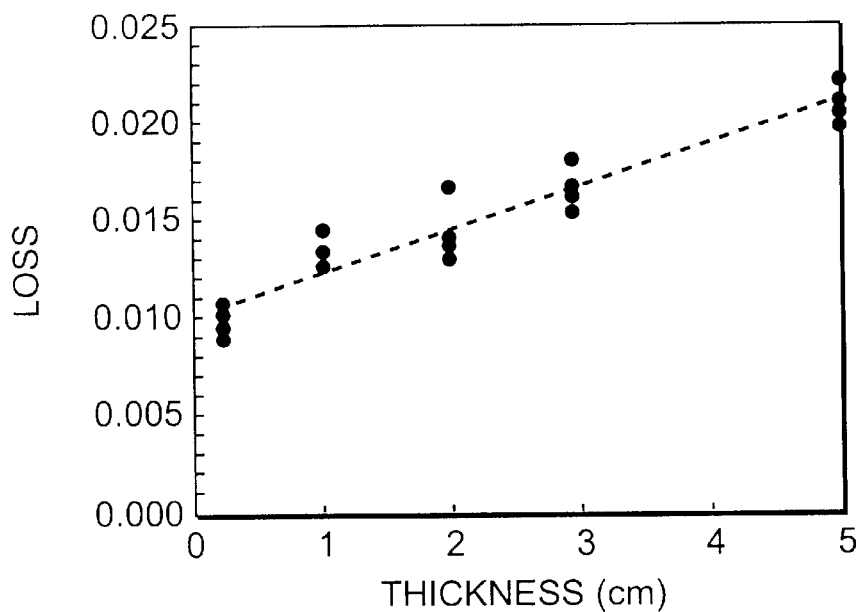
FIG. 4 is a plot showing the loss of the calibration samples versus the sample thickness.

Here, Tth is the theoretical transmittance that is a characteristic of the material of the calibration samples. Once the relationship between the sample thickness and the loss has been obtained using Equation (2), a second plot is prepared by plotting these results on a coordinate plane with the sample thickness plotted on the horizontal axis and the loss plotted on the vertical axis. A series of points plotted in this second plot can be fitted using a straight line (e.g., as shown in FIG. 4). This straight line increases (i.e., has a positive slope) with an increase in the sample thickness. The slope of this straight line defines a bulk loss coefficient $\beta$ (/cm) of the calibration samples.

The transmittance values To of the respective calibration samples are expressed in terms of the bulk loss coefficient $\beta$ (/cm) obtained by means of the above procedure and the sample thickness L (cm), as follows:

$$To=Tth\times\exp(-\beta\times L) \qquad (3)$$

Assuming that the instrument errors can be eliminated by multiplying the transmittance Tc at the reference time tc (obtained by means of Equation (1)) by the calibration value $K_L$, we obtain the following Equation (4):

$$To=K_L\times Tc \qquad (4)$$

Then, the following Equation (5) is obtained from Equation (3) and Equation (4):

$$K_L=(Tth/Tc)\times\exp(-\beta\times L). \qquad (5)$$

Thus, $K_L$ is derived by determining the value of the transmittance corresponding to the reference time tc as Tc using the straight line fitting in the aforementioned first plot, and by substituting this value, the already determined bulk loss coefficient $\beta$, and correction sample thickness (=Lo) into Equation (5).

By these procedures, the calibration value $K_L$ of the spectrophotometer 10 corresponding to the material and the thickness (=Lo) of the evaluation sample M is determined.

Once the parameters of the transmittance decrease rate "a" and the limiting elapsed time "tm" corresponding to the material and the thickness (=Lo) of the evaluation sample M have been determined along with the calibration value $K_L$ of the spectrophotometer, as described above, the transmittance of the evaluation sample M (i.e., the true transmittance To) can be determined by the first through fourth steps shown in FIG. 1. This will be described next.

In order to determine the transmittance (true transmittance) To of the evaluation sample M, the evaluation sample M is first cleaned (this includes a drying process) as shown in FIG. 1 (first step). When this cleaning has been completed, the evaluation sample M is placed in the spectrophotometer 10, and the transmittance T is determined by performing a transmittance measurement within a specified time period determined from the known limiting elapsed time "tm" in accordance with the process described above (second step). Here, the evaluation sample M with respect to which cleaning has been completed is stored in a desiccator, and is removed from the desiccator only at the time of transmittance measurement (this is also true in cases where a plurality of evaluation samples are used). Once the transmittance T has been determined, the transmittance Tc at the reference time tc is obtained by substituting the value of the transmittance decrease rate "a" and the value of the elapsed time "t" at the point in time at which the transmittance T was measured into Equation (1) (third step). Once the reference transmittance Tc has been determined, a calibration is performed by means of Equation (4) using the calibration value $K_L$, which is already known as a result of the above-mentioned procedure, so that the true transmittance To is obtained (fourth step)

Thus, in the transmittance measurement method of the present invention, if the transmittance is measured within a specified time period following the completion of cleaning during which the transmittance decrease rate of the evaluation sample M remains a constant value, the measured transmittance value can be corrected (converted) to the transmittance at an arbitrarily selected evaluation time tc within the above-mentioned specified time period regardless of the elapsed time (elapsed time from the completion of cleaning) at which the transmittance measurement is performed. Accordingly, by setting the reference time (evaluation time) tc at an appropriate time, which is typically closer to the completion of cleaning, it is possible to determine an accurate transmittance value that is unaffected by the surface re-contamination that progresses after the completion of cleaning (i.e., unaffected by a transmittance drop). Accordingly, the transmittance measurement may be performed at any elapsed time as long as this elapsed time is within the above-mentioned specified time period. Thus, there is a time margin for the measurement of transmittance. Furthermore, in cases where there is a plurality of evaluation samples, a procedure can be used in which all of these samples are cleaned at the same time, after which successive transmittance measurements are performed. Accordingly, the time required for the evaluation of transmittance can be greatly saved.

Furthermore, in the preferred embodiment described above, since a spectrophotometer 10 with a relatively poor measurement precision was used to determine the transmittance T of the evaluation sample, it was necessary to correct the transmittance Tc at the desired time tc to the true transmittance To.

Once the true transmittance To is obtained as described above, it is also possible to determine the bulk loss coefficient $\beta$ of the evaluation sample M by the following Equation (6), which is obtained by modifying Equation (3):

$$\beta = -LN(To/Tth)/L \qquad (6)$$

By thus determining the bulk loss coefficient $\beta$ of the evaluation sample M, the bulk absorption coefficient of the evaluation sample M can also be determined. By evaluating this bulk absorption coefficient, it is possible to determine whether or not the evaluation sample is suitable for use in the optical system in question.

Working Examples

Below, working examples of the measurement method according to the present invention will be described. However, the evaluation method of the present invention is not limited to the following example.

In this working example, the transmittance values were determined for three evaluation samples A, B and C with the same shape (diameter 60 mm, thickness 10 mm), cut from three silica glass ingots, respectively, synthesized by the direct method with the synthesis conditions such as raw materials and combustion gases varied. The above-mentioned spectrophotometer 10 was used for the transmittance measurements. A D2 lamp (wavelength 193.4 nm) was used as the light source in both the spectrophotometer 10 and calibration transmittance measuring apparatus 50. Furthermore, the reference time (evaluation time) at which the evaluation of transmittance was performed was set at 5 minutes after the completion of cleaning (tc=5 minutes).

Before actual measurements were performed for the evaluation samples A, B and C, the calibration value $K_L$ of the spectrophotometer 10 to be used for the measurements was determined. This was accomplished as follows: First, five calibration samples with thicknesses of 5, 10, 20, 30 and 50 mm, respectively, were prepared from synthetic silica glass ingots synthesized by the direct method in the same manner as that for the above-mentioned evaluation samples. These calibration samples were polished such that the degree of parallel orientation of two mutually opposed polished surfaces was within 10 seconds or better, so that the flatness of each surface was three Newton rings or better, and that the surface roughness RMS of each surface was 10 angstroms or less. Furthermore, a finish polishing using a high-purity $SiO_2$ powder was performed so that no polishing agent that would cause surface absorption remained on the surfaces.

Next, the above-mentioned calibration samples were cleaned with IPA (isopropyl alcohol). The IPA cleaning is a type of wet cleaning, and involves a series of cleaning and drying processes in which contaminant substances are removed by means of a chemical solution, etc., and the remaining chemical solution, etc., on the sample surface is washed away by high-grade pure water, etc., after which the sample is held in an IPA vapor and then dried by taking it out. Since these cleaning and drying processes are performed in a high-purity IPA vapor, a special feature of this process is that surfaces with a high degree of cleanness are obtained. The bulk loss coefficient $\beta$ of these calibration samples that were subjected to IPA cleaning was measured using the above-mentioned calibration transmittance measuring apparatus 50, and the losses were determined for the respective sample thicknesses. The results are shown in FIG. 4 (corresponding to the above-mentioned second plot). Furthermore, measurements were performed a plurality of times for each calibration sample. These plotted points shown in FIG. 4 were fitted with a straight line (indicated by the dotted line in FIG. 4), and a bulk loss coefficient of $\beta=0.0020$/cm was obtained from the slope of this line.

Figure 5:
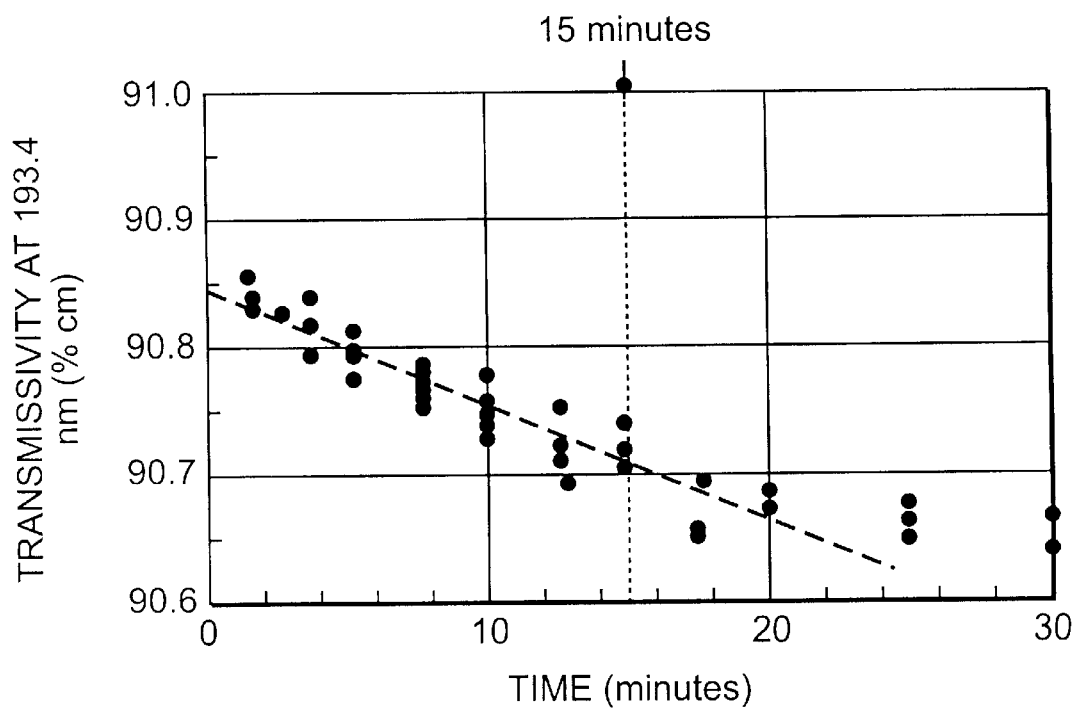
FIG. 5 is one example of a plot showing the transmittance of the correction samples versus the elapsed time from the completion of cleaning.

Next, among the above-mentioned calibration samples, the calibration samples with a thickness of 10 mm were used as correction samples (since the thickness of the evaluation samples A, B and C was 10 mm), and the relationship between the transmittance T and the elapsed time t was determined by repeatedly performing cleaning and transmittance measurements. The results are shown in FIG. 5 (corresponding to the above-mentioned first plot). As seen from FIG. 5, the transmittance linearly decreases with an increase in the elapsed time up to an elapsed time of about 15 minutes (i.e., the limiting elapsed time "tm"=15 minutes). These plotted points up to the elapsed time of 15 minutes from the completion of cleaning were fitted by means of a straight line. However, when the elapsed time exceeds 15 minutes, the plotted points deviate from the straight line, and the rate of change becomes more gradual than that seen up to the elapsed time of 15 minutes. Furthermore, a transmittance decrease rate "a" of 0.009 (%/min) is obtained from the slope of this straight line. The transmittance (Tc) corresponding to the reference (evaluation) time tc of 5 (minutes) was determined from this FIG. 5 to yield a value of Tc=90.80 (%). Accordingly, the calibration value $K_L$ of the spectrophotometer 10 for an evaluation sample thickness L of 10 mm and the reference time tc of 5 (minutes) is determined as shown in the following Equation (7) from Equation (5), with the theoretical transmittance Tth set at 90.8748 (%).

$$K_L = (90.8748/90.80)\exp(-0.0020 \times 10) = 0.99882 \qquad (7)$$

Here, the fact that $K_L < 1$ indicates that the transmittance T measured by the spectrophotometer 10 is higher than the true transmittance To. Accordingly, in cases where no calibration is performed, a transmittance that is higher than the actual transmittance would be obtained. In cases where such a member is used in the optical system of a stepper, etc., there is a danger of an unexpected drop in the transmittance.

Further, the precision of the correction/calibration procedure described above was investigated. Thirty (30) samples were cut from more or less the same positions in ingots synthesized by the direct method in the same manner as in the case of the above-mentioned calibration samples. These samples were finished into samples with a diameter of 60 mm and a thickness of 10 mm, and were polished in the same manner as the above-mentioned calibration samples. Then, the transmittance values T of all of these samples were measured while the elapsed time from the completion of cleaning was monitored, and these transmittance values T were corrected to the values at the reference time tc=5

Figure 6:
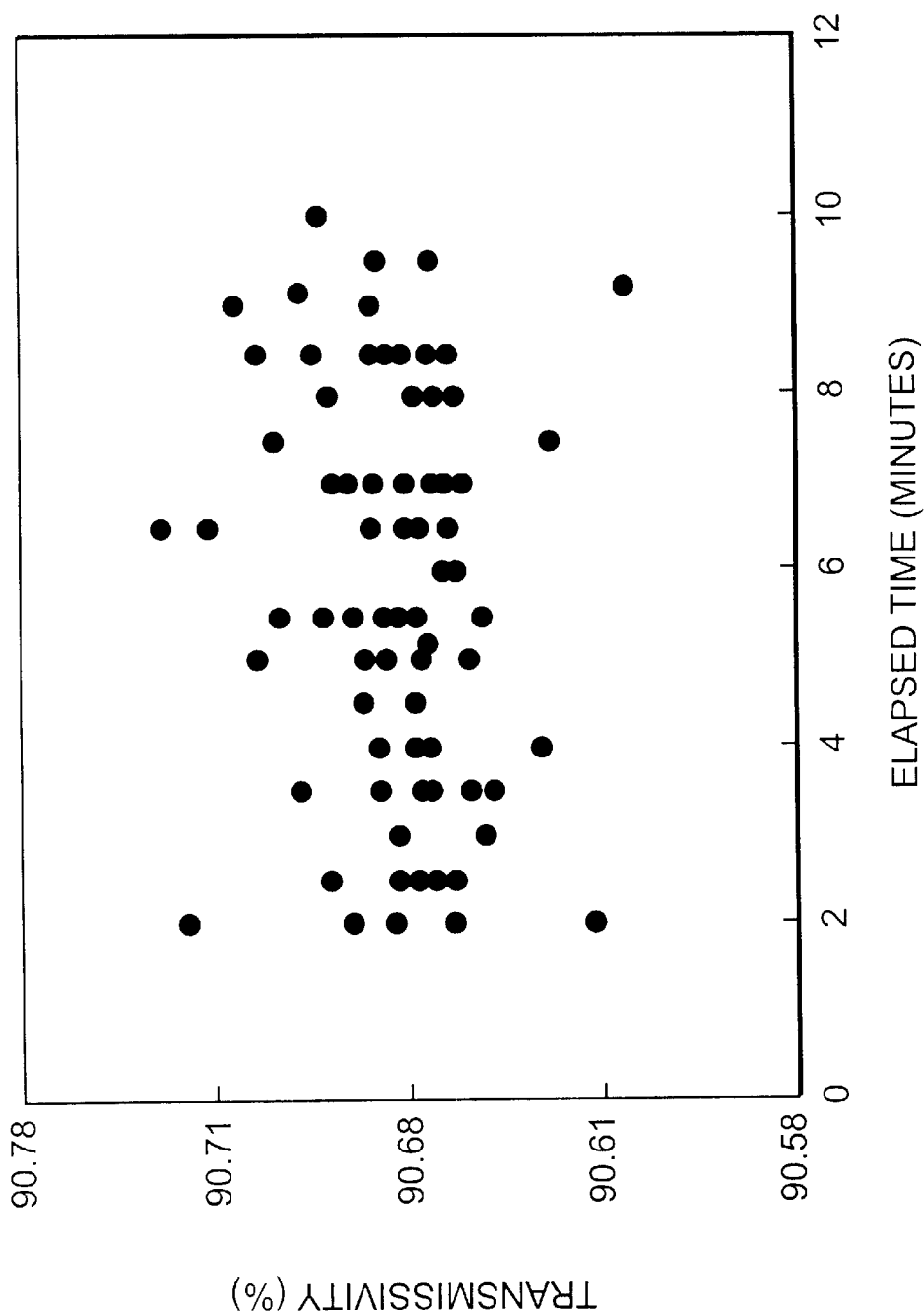
FIG. 6 is a plot showing the precision of correction/calibration in the present preferred embodiment. Here, the transmittance values of the corrected/calibrated samples are plotted with the elapsed time at which the transmittance was measured prior to the correction/calibration.

(minutes) using the already determined value of the transmittance decrease rate (a=0.009%/cm) and Equation (1). Then, a calibration was performed for each sample using the already determined calibration value ($K_L$=0.99882). In FIG. 6, the transmittance values thus obtained (corrected/calibrated transmittance values) are plotted against the elapsed time t at which the transmittance values prior to correction/calibration were measured. As seen from FIG. 6, the corrected/calibrated transmittance values are approximately constant regardless of the elapsed time t. Furthermore, the bulk absorption coefficients for the respective samples were calculated using Equation (8) shown below, and the fluctuations (standard deviation) was determined. Here, the internal scattering coefficient was set at 0.0015/cm. The variation was determined to be 0.0002/cm. Thus, it can be said that a sufficient precision was obtained in determining the bulk absorption coefficient of 0.001/cm.

$$\text{Bulk Absorption Coefficient} = \quad (8)$$
$$\text{Bulk Loss Coefficient } (\beta) - \text{Internal Scattering Coefficient}$$

the other hand, as seen from the results for sample A, when these values are corrected/calibrated to transmittance values at the reference time, even the transmittance values obtained at different elapsed times show good approximate agreement.

Furthermore, referring to the bulk absorption coefficients obtained through the correction/calibration, it is seen that the value for sample A is small, i.e., less than 0.0010/cm. Thus, this sample can be characterized as suitable for use in the optical system of an excimer stepper (judgment of "O" in Table I). In the case of sample B, the value is 0.0012/cm; however, since the variation of the bulk absorption coefficient calculated in this working example was found to be as much as 0.0002/cm, this sample may not be suitable for use in the optical system of an excimer stepper, as explained above (evaluation of "Δ" in Table I). In the case of sample C, the bulk absorption coefficient greatly exceeds 0.001 0/cm. Accordingly, it can be said that this sample is unsuitable for use in the optical system of an excimer stepper ("X" in Table I).

TABLE I

| Sample Name | Measurement Time (minutes) | Measured Transmissivity Value (%) | Bulk Absorption Coefficient (No Calibration) (/cm) | Transmissivity Tc (After Time Correction) (%) | Transmissivity To (After Calibration) (%) | Bulk Absorption Coefficient (After Calibration) (/cm) | Evaluation Result |
|---|---|---|---|---|---|---|---|
| A | 2 | 90.82 | −0.00095 | 90.79 | 90.69 | 0.0005 | O |
| A | 7.5 | 90.78 | −0.00051 | 90.80 | 90.70 | 0.0004 | O |
| B | 6.5 | 90.72 | 0.00015 | 90.73 | 90.63 | 0.0012 | Δ |
| C | 4 | 90.73 | 0.00004 | 90.72 | 90.61 | 0.0013 | x |

Next, the transmittance values To of the evaluation samples A, B and C were actually determined. The evaluation samples A, B and C were polished in the same manner as the above-mentioned calibration samples, and the three samples were subjected to the IPA cleaning and drying together. Thereafter, transmittance measurements were performed using the spectrophotometer 10 while monitoring the elapsed time t from the completion of cleaning. The transmittance values T thus obtained were corrected to transmittance values Tc at the reference time tc of 5 (minutes) by means of Equation (1) using the already determined transmittance decrease rate (a=0.009%/min). Then, these transmittance values Tc were calibrated by means of Equation (4) using the already determined calibration value $K_L$, thus producing the corrected/calibrated transmittance values To. Furthermore, the bulk loss coefficients β were calculated for the respective evaluation samples from Equation (6), and the bulk absorption coefficients were determined by means of the above-mentioned Equation (8). Here as well, the internal scattering coefficient was set at 0.0015/cm.

The results are listed in Table I below. As seen from the results of sample A in Table I, inaccurate results in which the bulk absorption coefficients show negative values were obtained in cases where no correction/calibration was performed. Furthermore, it is seen from the results for sample A that if the measurement time differs by 5.5 minutes, a difference of about 0.0004/cm appears in the bulk absorption coefficient obtained without calibration, indicating that the effect of surface contamination following the completion of cleaning cannot be ignored in a case where a bulk absorption difference in the order of 0.001/cm needs to be evaluated. On In the method for measuring the transmittance of optical members for ultraviolet use according to the present invention, as described above, if transmittance measurements are performed within a specified time period following the completion of cleaning during which the rate of the drop in transmittance of an object of measurement (optical member for ultraviolet use) remains constant, the measured transmittance values can be corrected (converted) to transmittance values at an arbitrarily selected evaluation time within the above-mentioned specified time period regardless of the elapsed time (measurement time; elapsed time from the completion of cleaning) at which the above-mentioned transmittance measurements are performed. Accordingly, if the above-mentioned reference time is set at an appropriate time that is close to the completion of cleaning, accurate transmittance values can be determined without adverse effects from surface contamination that develops after the completion of cleaning, i.e., without transmittance drop. Accordingly, transmittance measurements may be performed at any elapsed time as long as this elapsed time is within the above-mentioned specified time period, so that there is a time margin for the measurement of transmittance. Furthermore, in cases where there are a plurality of objects of measurement, a procedure may be used in which all of these objects of measurement are cleaned at the same time, and thereafter transmittance measurements are performed successively. Accordingly, the time required for the evaluation of transmittance can be greatly saved.

Synthetic Silica Glass and Photolithography Apparatus

As described above, the conventional synthetic silica glass has a drawback of bulk-absorption shortly after irradiation. To elucidate the causes of the bulk-absorption shortly after irradiation of ultraviolet light by silica glass, the present inventors investigated the relationship between various physical properties of silica glass and the magnitude of the bulk-absorption shortly after irradiation that occurs. As a result, it was found that if a reducing atmosphere that is stronger than necessary is provided when silica glass is synthesized in the reducing atmosphere in order to dope hydrogen molecules into the glass, which is a factor that improves durability, the ≡Si—H structural defects, which cause a drop in the transmittance of the resulting silica glass members (such structural defects are easily cleaved by ultraviolet irradiation at a low energy density to form the E' centers), are formed in large quantities in the silica glass produced. That is, there is a stronger tendency for the bulk-absorption shortly after irradiation to appear in silica glass with a larger hydrogen molecule content.

Specifically, a synthetic silica glass of the present invention is obtained by appropriately controlling the hydrogen molecule concentration of the silica glass to a proper value during synthesis in a reducing atmosphere, so that the concentration of ≡Si—H contained in the glass at the time of synthesis is decreased. This glass is characterized in that when the glass is irradiated with $1 \times 10^4$ pulses of irradiation by an ArF excimer laser at an energy density of 0.1 $\mu J/cm^2 \cdot p$ to 200 $mJ/cm^2 \cdot p$, the loss coefficient measured at 193.4 nm following the irradiation is about 0.0050 $cm^{-1}$ or less. Furthermore, in a photolithographic apparatus of the present invention, some or all of the optical members (e.g., the collimator lens 12, fly-eye lens 13, condenser lens 14 and projection lenses 22, etc., in the example of FIG. 7, which will be explained below) are constructed from synthetic silica glass members having such characteristics.

As a result of some or all of the optical members of the above-mentioned photolithography apparatus (e.g., the stepper 1 in the example of FIG. 7 below) being constructed from the synthetic silica glass members of the present invention, a high transmittance can be maintained even when the light source used is an ArF excimer laser, so that superior practical utility can be obtained. Furthermore, such synthetic silica glass members are obtained from a glass in which the hydrogen molecule concentration is in the range of about $1 \times 10^{16}$ molecules/cm³ to about $5 \times 10^{18}$ molecules/cm³, and the loss coefficient prior to irradiation with ultraviolet light is about 0.0020 $cm^{-1}$ or less.

Preferred Embodiment

Figure 7:
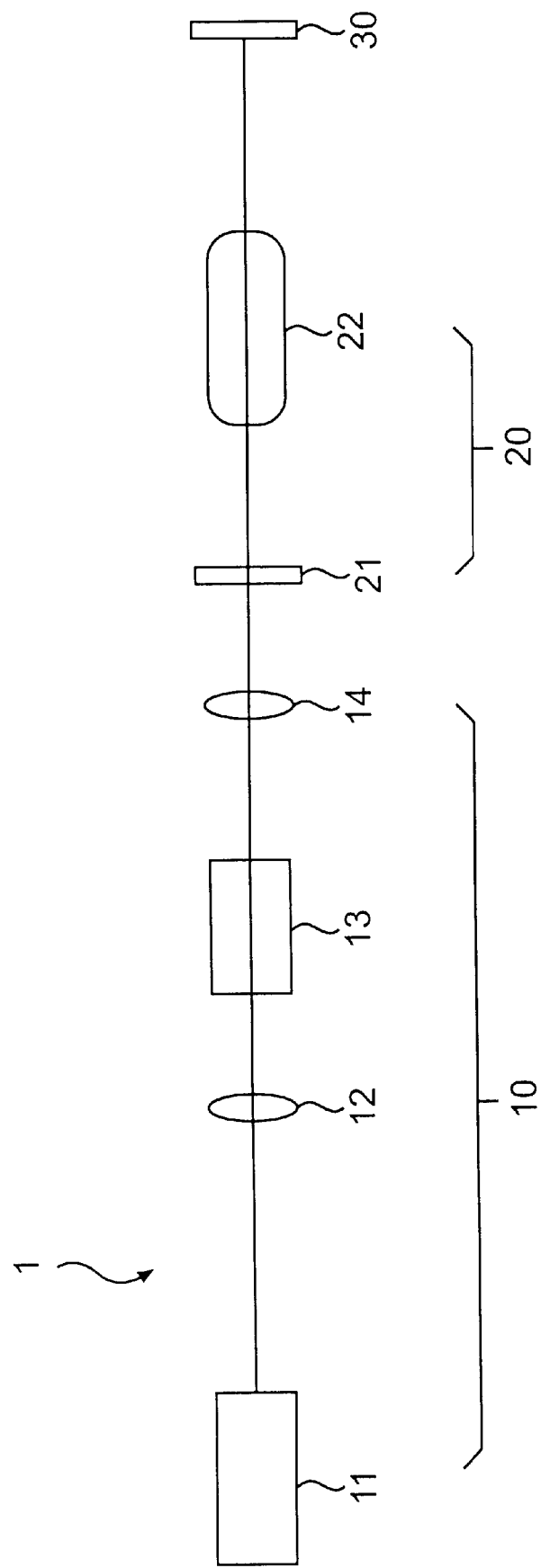
FIG. 7 is a schematic diagram which shows an example of the construction of a photolithography apparatus according to the present invention.

A preferred embodiment of the synthetic silica glass and the photolithography apparatus according to the present invention will be described below with reference to the attached figures. FIG. 7 shows the construction of a stepper 1 according to a preferred embodiment of the photolithographic apparatus of the present invention. The stepper 1 is constructed from an illumination optical system 10, which uniformly illuminates a reticle 21 with ultraviolet light emitted from a light source 11, and a projection optical system 20, which reduces the integrated circuit pattern formed on the reticle 21 to ¼ or ⅕ of the original size, and projects this pattern onto a wafer 30.

In addition to the above-mentioned light source 11, the illumination optical system 10 has a collimator lens 12, a fly-eye lens 13 and a condenser lens 14. The projection optical system 20 has the reticle 21 and a projection lens system 22 (reducing projecting lens) consisting of a plurality of lenses.

The light emitted from the light source 11 is converted into parallel light by the collimator lens 12, and the intensity of the light is made uniform by the fly-eye lens 13. Thereafter, the light reaches the reticle 21 after being focused by the condenser lens 14. The light passing through the reticle 21 reaches the wafer 30 after being focused by the projection lens 22. As a result, the integrated circuit pattern on the reticle 21 is reduced and exposed on the wafer 30.

Here, the lens members of the collimator lens 12, fly-eye lens 13, condenser lens 14, and projection lenses 22 (as well as other lens and mirror members not indicated in the figure) are constructed from synthetic silica glass. Some or all of these synthetic silica glass members have characteristics such that when the glass members are irradiated with $1 \times 10^4$ pulses of irradiation by an ArF excimer laser at an energy density of 0.1 $\mu J/cm^2 \cdot p$ to 200 $mJ/cm^2 \cdot p$, the loss coefficient measured at 193.4 nm following irradiation is about 0.0050 $cm^{-1}$ or less.

Synthetic silica glass members, which have such characteristics, are obtained from a glass in which the hydrogen molecule concentration is in the range of about $1 \times 10^{16}$ molecules/cm³ to about $5 \times 10^{18}$ molecules/cm³, and the loss coefficient prior to irradiation with ultraviolet light is about 0.0020 $cm^{-1}$ or less (see the working examples and comparative examples, which will be described below). The process by which such synthetic silica glass members are obtained will be described below.

Figure 8:
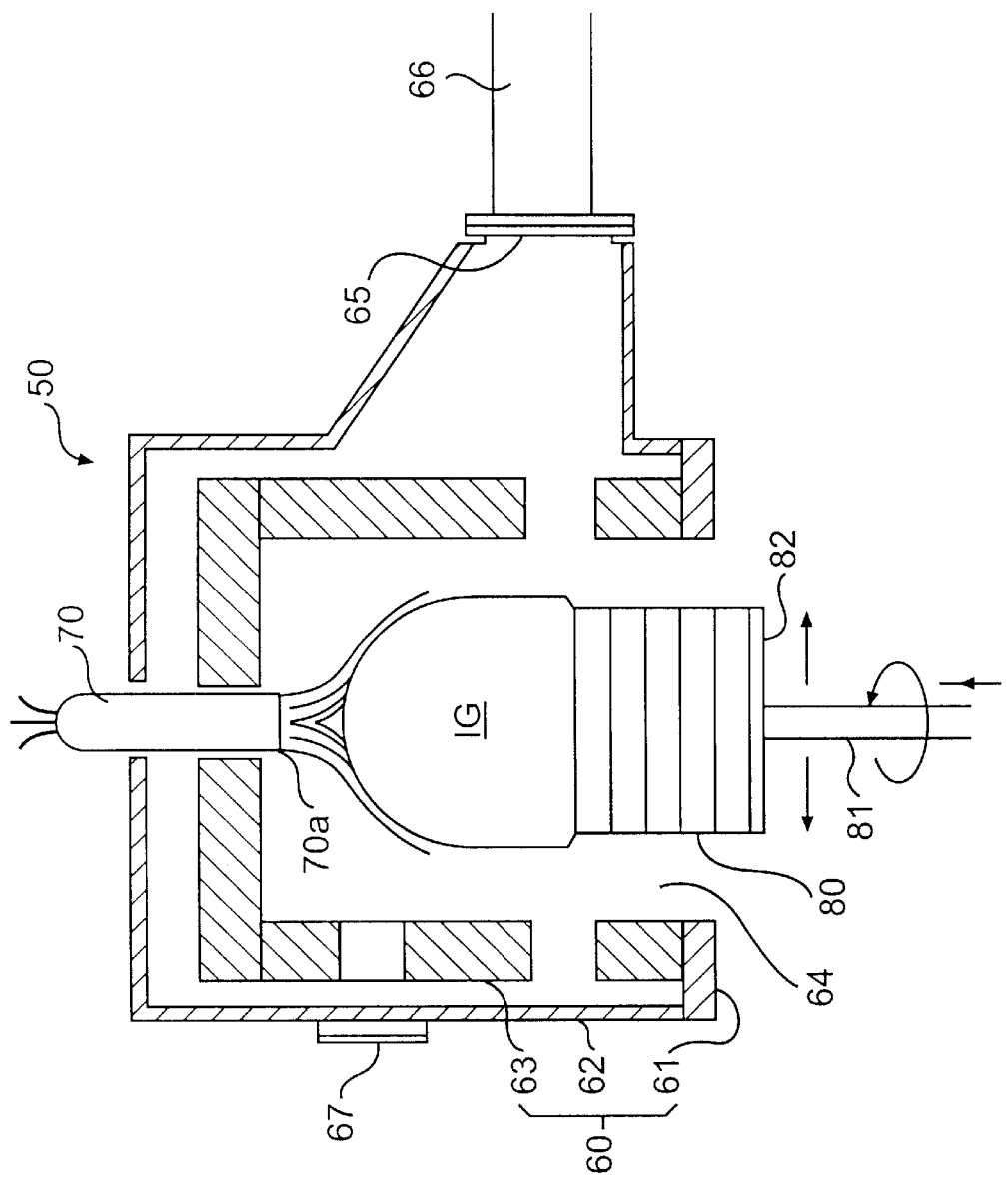
FIG. 8 is a schematic sectional view which shows an example of a synthetic silica glass manufacturing apparatus according to the present invention.

FIG. 8 shows an example of an apparatus used to manufacture a synthetic silica glass ingot, which serves as a basis for such synthetic silica glass members. As shown in the figure, this synthetic silica glass manufacturing apparatus 50 is constructed of a furnace 60, a burner 70 disposed in the upper part of the furnace 60, and a target 80 disposed beneath the burner 70 in a furnace internal space 64 of the furnace 60. The furnace 60 is constructed of a refractory material 63 disposed inside a furnace frame 62, which is in turn installed on a furnace floor plate 61, and the burner 70 is installed so as to pass through the upper portion of the furnace frame 62 and refractory material 63. As will be described later, the burner 70 has a multi-tube structure, and the nozzle 70a of the burner 70 faces downward—i.e., toward the furnace internal space 64. The target 80 is constructed of a plurality of opaque silica glass plates stacked in a vertical configuration. The target 80 is placed on the upper surface of a horizontal disk 82, which is installed on the upper part of a supporting rod extending in the vertical direction so that the uppermost surface of the target 80 faces the nozzle 70a of the burner 70. An exhaust port 65, which is used to discharge waste gases, such as HCl, generated inside the furnace 60 during the synthesis of the silica glass, is formed in the furnace frame 62. An exhaust tube 66, which communicates with the outside air, is connected to the exhaust port 65. Furthermore, a window 67, which is used to observe the furnace internal space 64 from the outside, is formed in the outer wall of the furnace 62.

Figure 9:
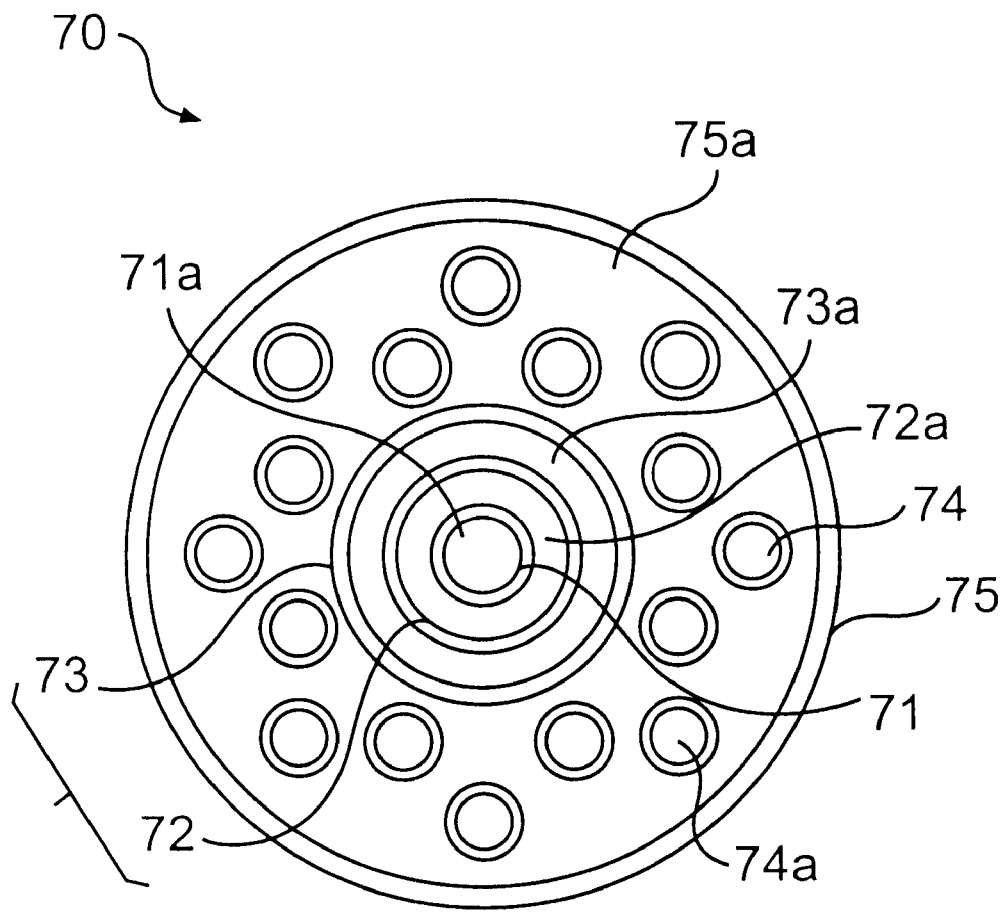
FIG. 9 is a plan view of a burner in the manufacturing apparatus of FIG. 8, as seen from the side of the nozzles.

FIG. 9 shows the burner 70 as seen from the side of the nozzle 70a. A raw material nozzle 71, oxygen/hydrogen nozzles 72 and 73, oxygen nozzles 74, and a hydrogen nozzle 75 are installed in that order from the center to the periphery. The raw material nozzle 71 is positioned at the center of the burner 70 from which the raw material of silicon tetrachloride ($SiCl_4$) and a carrier gas (usually oxygen) for diluting the silicon tetrachloride are emitted from the internal space 71a of the raw material nozzle 71. The two oxygen/hydrogen nozzles 72 and 73 are disposed in a concentric arrangement so as to surround the raw material nozzle 71, and oxygen gas and/or hydrogen gas is emitted from the respective internal spaces 72a and 73a of these tubes. A plurality of oxygen nozzles 74 are positioned to the outside of the oxygen/hydrogen nozzle 73, and oxygen gas is emitted from the respective internal spaces 74a of these tubes 74. Furthermore, the hydrogen nozzle tube 75 is positioned concentrically with raw material nozzle 71 and with oxygen/hydrogen nozzles 72 and 73 so as to surround the oxygen nozzles 74, and hydrogen gas is emitted from the internal space 75a of the tube 75. The oxygen gas and hydrogen gas are emitted from separate tubes in this manner in order to ensure that these gases react uniformly during the synthesis of the silica glass.

The synthesis of the silica glass is conducted by burning the raw material, oxygen and hydrogen while emitting these gases towards the upper surface of the target 80 from the burner 70. As a result, the silicon tetrachloride reacts with the oxygen and hydrogen (i.e., undergoes hydrolysis), and a powder of the synthesized silica glass is deposited on the target 80. Then, a synthetic silica glass ingot IG is formed by vitrification of this powder. Here, in order to ensure that the composition of the ingot IG thus produced achieves an overall uniformity, the supporting rod 81 is driven during the synthesis process such that the target 80 is rotated about its central axis at a specified speed, and oscillates in the horizontal direction at a fixed time interval at the same time. Furthermore, the target 80 in its entirety is drawn downwards at a specified speed so that the spacing between the upper end of the ingot IG under formation and the nozzle 70a of the burner 70 always remains constant.

By the procedure described above, a synthetic silica glass ingot is produced. Because hydrogen molecules may be introduced during synthesis and may be released during a heat treatment, the concentration of hydrogen molecules contained in the resultant synthetic silica glass produced can be controlled by adjusting the synthesis conditions (e.g., the proportion of oxygen gas and hydrogen gas supplied from the burner 70) and the heat treatment conditions (e.g., the presence or absence of the heat treatment process, etc.). In the present invention, these conditions are adjusted so that the concentration of hydrogen molecules contained in the ingot is (in the range of about $1 \times 10^{16}$ molecules/cm$^3$ to about $5 \times 10^{18}$ molecules/cm$^3$. The concentration of hydrogen molecules in the synthetic silica glass ingot can be measured by the Raman spectroscopy, for example.

Once a synthetic silica glass ingot with a specified hydrogen molecule concentration has been obtained, a heat treatment may be performed. As an example of such a heat treatment may include the steps of maintaining the thus produced ingot at a constant temperature for a specified period of time; lowering the temperature at a specified temperature decreasing rate to a specified temperature; and leaving the ingot at a room temperature to cool it down. Following the completion of such a heat treatment, cutlets of a size corresponding to the size of desired synthetic silica glass members are cut out from the resultant ingot and polished. Then the cutlets are further finished to have specified dimensions by precision polishing using $SiO_2$, etc.

In this way, synthetic silica glass members, which have specified dimensions and a specified composition (i.e., a hydrogen molecule concentration in the range of about $1 \times 10^{16}$ molecules/cm$^3$ to about $5 \times 10^{18}$ molecules/cm$^3$) are obtained. Among these members, the members that have a loss coefficient of 0.0020 cm$^{-1}$ prior to irradiation with ultraviolet light are selected.

In this preferred embodiment, as a method for measuring the loss coefficient of the synthetic silica glass members prior to irradiation with ultraviolet light, the method described with reference to FIG. 1 above is used.

In most cases, when the synthetic silica glass, which has a hydrogen molecule concentration of about $1 \times 10^{16}$ molecules/cm$^3$ to about $5 \times 10^{18}$ molecules/cm$^3$ and a loss coefficient (prior to ultraviolet irradiation) of about 0.0020 cm$^{-1}$ or less, manufactured as described above, is irradiated with $1 \times 10^4$ pulses of light by means of an ArF excimer laser at an energy density of 0.1 $\mu$J/cm$^2$·p to 200 mJ/cm$^2$·p, the loss coefficient measured at 193.4 nm following the irradiation becomes about 0.0050 cm$^{-1}$ or less. Synthetic silica glass that satisfies such conditions is selected and used in the above-mentioned stepper 1.

Thus, since all or some of the optical members, such as lenses, in the stepper 1 are synthetic silica glass members that have the above-mentioned characteristics, the apparatus as a whole has a high transmittance and shows superior practical utility even in cases where the light source 11 is a light source with a short wavelength of about 200 nm or less, such as an ArF excimer laser. Furthermore, it goes without saying that a high transmittance is also ensured in cases where the light source 11 of the stepper 1 is changed to a light source that emits light with a longer wavelength than that of an ArF excimer laser, so that the resultant apparatus has sufficient practical utility.

Working Examples

Working examples (and comparative examples) of the present invention will be described below. However, the present invention is not limited to the working examples described here.

First, five types of synthetic silica glass ingots were manufactured using the above-mentioned synthetic silica glass manufacturing apparatus 50, with the synthesis conditions—such as the raw material flow rate and oxygen gas/hydrogen gas flow rate ratio—varied. Then, some of the ingots manufactured were subjected to a heat treatment, which involves the steps of maintaining the ingots at a temperature of 1000° C. for 10 hours, lowering the temperature to 500° C. or less at a temperature lowering rate of 10° C. per hour or less, and leaving the ingots at a room temperature to cool down. Next, cutlets with a diameter of 60 mm and a thickness of 10 mm were cut from these ingots and were subjected to precision polishing to produce 13 evaluation samples. Then, after the transmittance values of these samples prior to irradiation were calculated using the method described above, the hydrogen molecule concentrations of the respective samples were measured by the Raman spectroscopy method. In more detail, this measurement was performed by measuring the Raman scattering intensities at 800 cm$^{-1}$ and at 4135 cm$^{-1}$ to derive the ratio of these intensities using the method described by V. S. Khotimchenko et al., *J. Appl. Spectrosc.*, 46, 632–635 (1987), which is hereby incorporated by reference. Thereafter, the samples were irradiated with $1 \times 10^4$ pulses of light from an ArF excimer laser at various energy density values ranging form 0.1 ηJ/cm$^2$·p to 200 mJ/cm$^2$·p, and the transmittance at a wavelength of 193.4 nm after the irradiation was measured. After the transmittance was measured for the respective samples, the loss coefficients of the respective samples after ArF excimer laser irradiation were calculated using Equation (6). Here, the theoretical transmittance in Equation (6) was set at 90.8748 (%) as the value for synthetic silica glass at a wavelength of 193.4 nm.

Figure 10:
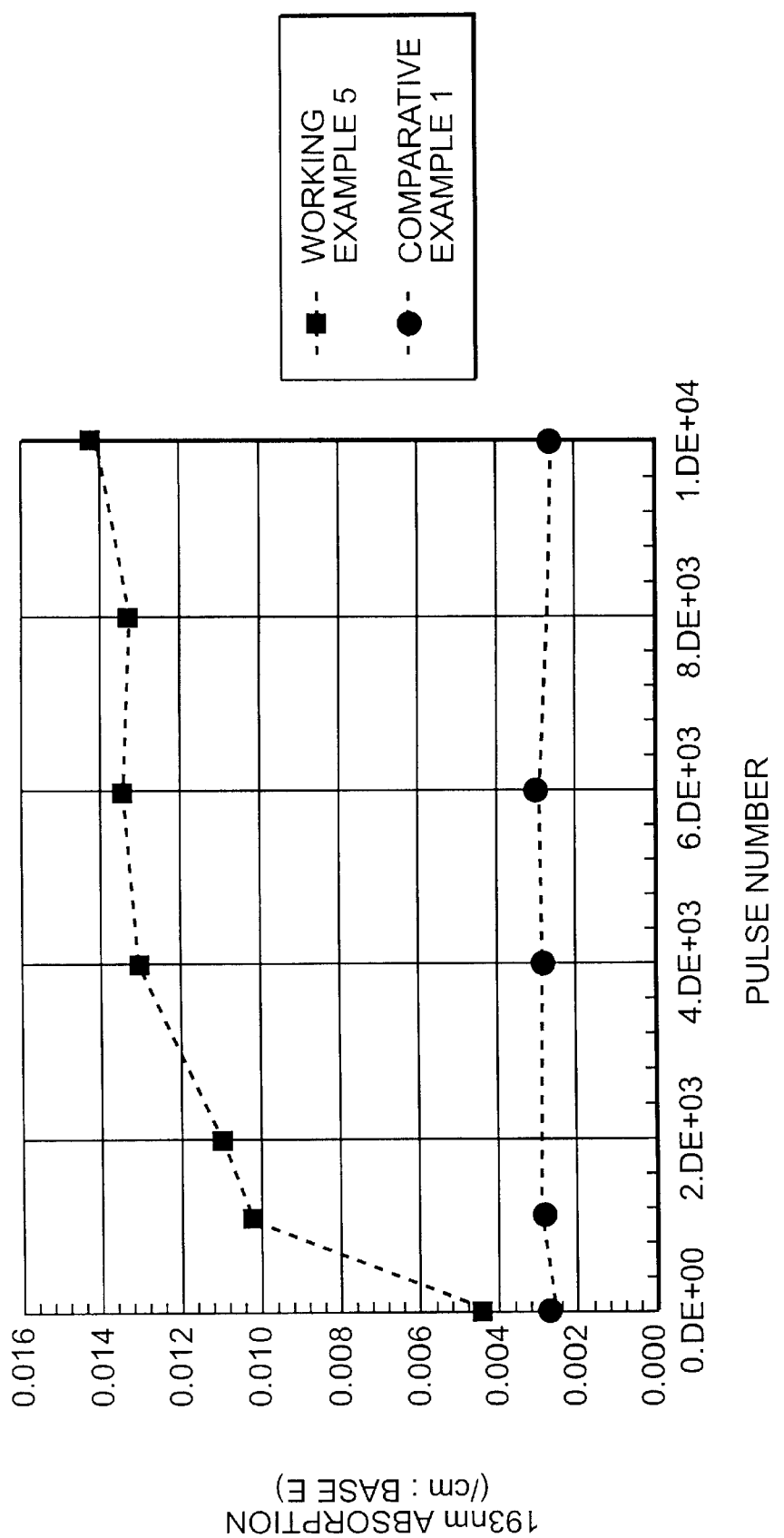
FIG. 10 shows changes of the loss coefficient versus the number of pulses of irradiation for samples corresponding to Working Example 5 and Comparative Example 1.
Figure 11:
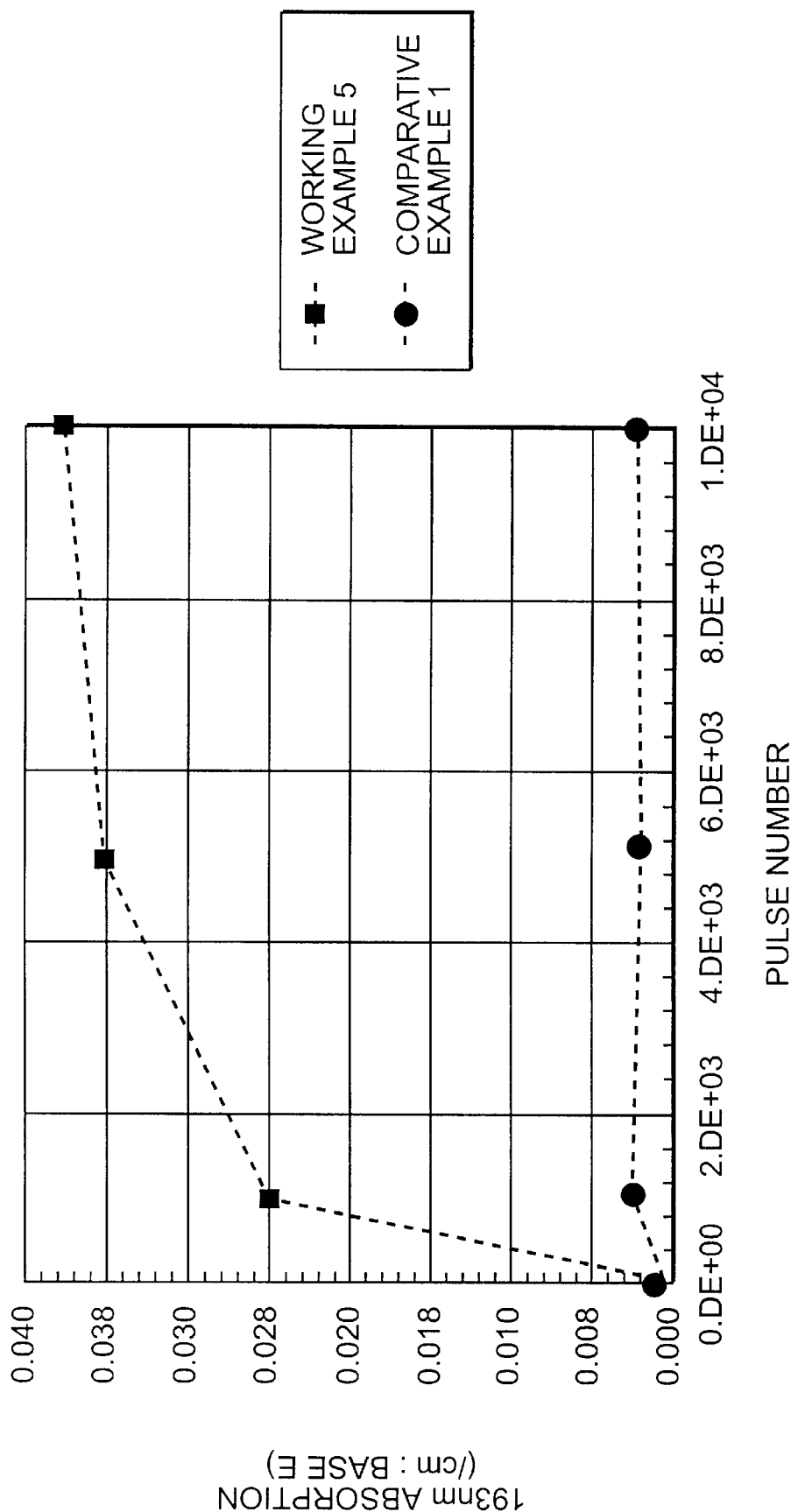
FIG. 11 shows changes of the loss coefficient versus the number of pulses of irradiation for samples corresponding to Working Example 8 and Comparative Example 3.

The results of the loss coefficients before and after the ArF excimer laser irradiation are shown in Table II below. FIG. 10 shows changes in the loss coefficient with the number of irradiating pulses when the ArF excimer laser irradiation was performed at an energy density of 2 mJ/cm$^2$·p (this corresponds to Working Example 5 and Comparative Example 1). FIG. 11 shows changes in the loss coefficient with the number of irradiating pulses when the ArF excimer laser irradiation was performed at an energy density of 200 mJ/cm$^2$·p (this corresponds to Working Example 8 and Comparative Example 3). As seen from Table II, the loss coefficient after the ArF excimer laser irradiation was 0.005 cm$^{-1}$ or less for the samples in which the hydrogen molecule concentration was in the range of about 1×10$^{16}$ molecules/cm$^3$ to about 5×10$^{18}$ molecules/cm$^3$ and the loss coefficient prior to the ultraviolet irradiation was 0.0020 cm$^{-1}$ or less.

graphic apparatus are constructed using such a synthetic silica glass, the transmittance of the photolithographic apparatus can be increased, and sufficient practical utility can be obtained even in cases where an ArF excimer laser is used as the light source.

It will be apparent to those skilled in the art that various modifications and variations can be made in the method for measuring the transmittance of synthetic silica glass, a

TABLE II

| | Raw Material Flow Rate (g/min) | (Oxygen Gas)/ (Hydrogen Gas)/ Flow Rate | Heat Treatment | Loss Coefficient Prior to Irradiation (/cm) | Hydrogen Concentration (molecules/cm$^3$) | Energy Density of ArF Irradiation (mJ/cm$^2$·p) | Loss Coefficient After Irradiation (/cm) | Evaluation Result |
|---|---|---|---|---|---|---|---|---|
| Working Example 1 | 30 | 0.385 | Present | 0.0016 | 1.6 × 10$^{18}$ | 0.2 | 0.00078 | ○ |
| Working Example 2 | 30 | 0.385 | Present | 0.0013 | 1.6 × 10$^{18}$ | 0.5 | 0.0018 | ○ |
| Working Example 3 | 30 | 0.382 | Present | 0.0015 | 1.1 × 10$^{18}$ | 0.7 | 0.0014 | ○ |
| Working Example 4 | 30 | 0.385 | Present | 0.0011 | 1.6 × 10$^{18}$ | 1 | 0.0025 | ○ |
| Working Example 5 | 30 | 0.378 | Present | 0.0016 | 1.8 × 10$^{18}$ | 2 | 0.0025 | ○ |
| Working Example 6 | 30 | 0.385 | Present | 0.0014 | 1.6 × 10$^{18}$ | 10 | 0.005 | ○ |
| Working Example 7 | 30 | 0.386 | Present | 0.0014 | 1.5 × 10$^{18}$ | 100 | 0.0025 | ○ |
| Working Example 8 | 30 | 0.388 | Present | 0.0012 | 9.8 × 10$^{17}$ | 200 | 0.0025 | ○ |
| Comparative Example 1 | 45 | 0.246 | Absent | 0.0043 | 5 × 10$^{18}$ | 2 | 0.0142 | x |
| Comparative Example 2 | 45 | 0.246 | Present | 0.0047 | 5 × 10$^{18}$ | 200 | 0.0057 | x |
| Comparative Example 3 | 60 | 0.355 | Absent | 0.0011 | 6 × 10$^{18}$ | 200 | 0.0375 | x |

Next, the synthetic silica glass members having the same hydrogen molecule concentration and loss coefficient prior to ultraviolet irradiation as the above-mentioned samples were installed in the above-mentioned stepper 1, and whether practical performance requirements were satisfied (i.e., whether the performance of the stepper 1 was adequate) was investigated. The results are listed in Table II in the right-most column. Here, "○" indicates that the stepper performance was adequate when the example was installed in an ArF excimer stepper; and "x" indicates that the stepper performance was inadequate when the example was installed in the ArF excimer stepper. As shown in Table II, superior and satisfactory performances were obtained for Working Examples 1 through 8, in which the loss coefficient following the ArF excimer laser irradiation was 0.005 cm$^{-1}$ or less. However, practical performance requirements were found not to be satisfied in Comparative Examples 1 through 3, in which the loss coefficient following the ArF excimer laser irradiation was greater than 0.005 cm$^{-1}$. Also, it can be seen that when the hydrogen molecule concentration exceeded about 5×10$^{18}$/cm$^3$, as in the case of Comparative Example 3, the loss coefficient after the irradiation with 1×10$^4$ pulses of ArF excimer laser light becomes extremely large.

As described above, the synthetic silica glass member of the present invention has characteristics such that when the member is irradiated with 1×10$^4$ pulses of light from an ArF excimer laser at an energy density in the range of 0.1 μJ/cm$^2$·p to 200 mJ/cm$^2$·p, the loss coefficient at 193.4 nm measured following the irradiation is about 0.0050 cm$^{-1}$ or less. If some or all of the optical members of a photolithosynthetic silica glass, and a photolithography apparatus of the present invention without departing from the spirit or scope of the invention. Thus, it is intended that the present invention cover the modifications and variations of this invention provided they come within the scope of the appended claims and their equivalents.

What is claimed is:

1. A method for evaluating a transmittance of an optical member, which is an object of measurement, for ultraviolet use, the method comprising the steps of:

cleaning the object of measurement;

measuring a transmittance of the object of measurement within a predetermined time period from completion of the cleaning during which a rate of decrease in the transmittance of the object of measurement remains substantially constant; and correcting the transmittance measured in the step of measuring to a transmittance at an evaluation time arbitrarily selected within the predetermined time period in accordance with the constant rate of decrease in the transmittance and a time at which the transmittance is measured.

2. The method according to claim 1, further comprising the step of calibrating the transmittance at the evaluation time using a calibration value that substantially eliminates instrumental errors which may occur in the step of measuring the transmittance.

3. The method according to claim 2, wherein the step of calibrating includes the step of determining the calibration value using a calibration transmittance measuring apparatus.

4. The method according to claim 2, wherein the step of calibrating includes the step of determining the calibration value using a calibration transmittance measuring apparatus in which an angle of divergence of measurement light is about 10 milli-radians (0.57 degrees) or less.

5. The method according to claim 2, wherein the step of calibrating includes the step of determining the calibration value using a calibration transmittance measuring apparatus in which an atmosphere around a light path of measurement light is a vacuum.

6. A method for manufacturing a silica glass, comprising the steps of:
   synthesizing a silica glass ingot;
   heat-treating the silica glass ingot;
   cutting out a plurality of silica glass pieces from the heat-treated silica glass ingot;
   evaluating transmittances of the plurality of silica glass pieces, comprising the steps of:
      cleaning the plurality of silica glass pieces,
      for each of the plurality of silica glass pieces, measuring a transmittance of the silica glass piece within a predetermined time period from completion of the cleaning during which a rate of decrease in the transmittance of the silica glass piece remains substantially constant, and
      for each of the plurality of silica glass pieces, correcting the measured transmittance to a transmittance at an evaluation time arbitrarily selected within the predetermined time period in accordance with the constant rate of decrease in the transmittance and a time at which the transmittance is measured; and
   selecting silica glass pieces, from among the plurality of silica glass pieces, that have a loss coefficient of about 0.0050 cm$^{-1}$ or less as determined from the transmittance evaluated in the step of evaluating.

7. The method according to claim 6, wherein the steps of synthesizing a silica glass ingot and heat-treating the silica glass ingot result in a plurality of silica glass pieces having a hydrogen molecule concentration in the range of about $1 \times 10^{16}$ molecules/cm$^3$ to about $5 \times 10^{18}$ molecules/cm$^3$.

8. The method according to claim 6, wherein the step of selecting includes selecting silica glass pieces, among the plurality of silica glass pieces, that have a loss coefficient of about 0.0020 cm$^{-1}$ or less as determined from the transmittance evaluated in the step of evaluating.

9. A method for evaluating a transmittance of an optical member for ultraviolet use, the method comprising the steps of:
   cleaning a surface of the optical member;
   measuring a transmittance of the optical member with respect to ultraviolet light within a predetermined time from completion of the cleaning during which a rate of decrease in transmittance remains substantially constant; and
   deriving a transmittance of the optical member at an evaluation time arbitrarily selected within the predetermined time period from the transmittance measured in the step of measuring in accordance with the constant rate of decrease in transmittance and a time at which the transmittance is measured in the step of measuring.

10. The method according to claim 9, further comprising the step of determining the constant rate of decrease and the predetermined time.

11. The method according to claim 10, wherein the step of determining includes measuring transmittance with respect to the ultraviolet light of a plurality of optical members that are manufactured under manufacturing conditions substantially similar to those for the optical member to be evaluated such that the constant rate of decrease and the predetermined time period are determined in advance of the step of cleaning.

12. A method for a quality control in manufacture of a plurality of synthetic silica glass members, the plurality of synthetic silica glass members being manufactured under substantially similar manufacturing conditions, the method comprising the steps of:
   cleaning surfaces of the plurality of synthetic silica glass members;
   measuring the transmittances of the plurality of synthetic silica glass members within a predetermined time period from completion of the cleaning during which a rate of decrease in the transmittance remains substantially constant, at least some of the plurality of synthetic silica glass members being measured at different times; and
   for each of the plurality of synthetic silica glass members, converting the transmittance measured in the step of measuring to a transmittance at an evaluation time arbitrarily selected within the predetermined time period in accordance with a time at which the transmittance is measured in the step of measuring and the constant rate of decrease, the evaluation time being set to be the same for all of the plurality of synthetic silica glass members, thereby enabling evaluation of the transmittance without effects of different transmittance decreases due to the different times at which the transmittances are measured in the step of measuring.

13. The method according to claim 12, further comprising the step of determining the constant rate of decrease in the transmittance and the predetermined time period during which the transmittance decreases substantially linearly.

14. The method according to claim 13, wherein the step of determining includes measuring the transmittance of a plurality of synthetic silica glass members that are manufactured under manufacturing conditions substantially similar to those for the plurality of synthetic silica glass members to be evaluated such that the constant rate of decrease and the predetermined time period are determined in advance of the step of cleaning.

15. A method for selecting synthetic silica glass members that meet a predetermined standard from a plurality of synthetic silica glass members, the method comprising the steps of:
   cleaning surfaces of the plurality of synthetic silica glass members;
   measuring transmittances of the plurality of synthetic silica glass members within a predetermined time period from completion of the cleaning during which a rate of decrease in the transmittance remains substantially constant, at least some of the plurality of synthetic silica glass members being measured at different measurement times;
   for each of the plurality of synthetic silica glass members, converting the transmittance measured in the step of measuring to a transmittance at a fixed evaluation time substantially close to the time of the completion of the cleaning in accordance with a time at which the transmittance is measured in the step of measuring and the constant rate of the transmittance decrease, thereby extrapolating an initial transmittance; and
   selecting among the plurality of silica glass members silica glass members that meet the predetermined standard in accordance with the initial transmittance extrapolated in the step of converting.

16. The method according to claim 15, wherein each of the plurality of silica glass members from which the silica glass members are to be selected has a molecular hydrogen concentration of about $1\times10^{16}$ molecules/cm$^3$ to about $5\times10^{18}$ molecules/cm$^3$.

17. The method according to claim 15, wherein the step of selecting includes the steps of:
   for each of the plurality of synthetic silica glass members, converting the extrapolated initial transmittance to a loss coefficient; and
   choosing among the plurality of silica glass members silica glass members that have the loss coefficient less than a predetermined value as meeting the predetermined standard.

18. The method according to claim 15, wherein in the step of measuring the transmittance, the transmittance measurement is conducted with respect to light having a wavelength of less than about 400 nm.

19. The method according to claim 18, wherein in the step of measuring the transmittance, the transmittance measurement is conducted with respect to the light having the wavelength of 193.4 nm.

20. The method according to claim 15, wherein each of the plurality of silica glass members from which the silica glass members are to be selected has a molecular hydrogen concentration of about $1\times10^{16}$ molecules/cm$^3$ to about $5\times10^{18}$ molecules/cm$^3$,
   wherein in the step of measuring the transmittance, the transmittance measurement is conducted with respect to the light having a wavelength of 193.4 nm, and
   wherein the step of selecting includes the steps of:
   for each of the plurality of synthetic silica glass members, converting the extrapolated initial transmittance to a loss coefficient; and
   choosing among the plurality of silica glass members silica glass members that have the loss coefficient less than about 0.0020 cm$^{-1}$ as meeting the predetermined standard.

21. The method according to claim 15, further comprising the step of determining the constant rate of decrease in the transmittance and the predetermined time period during which the transmittance decreases substantially linearly.

22. The method according to claim 21, wherein the step of determining includes measuring the transmittance of a plurality of synthetic silica glass members that are manufactured under manufacturing condition substantially similar to those for the plurality of synthetic silica glass members to be evaluated to determine the constant rate of the transmittance decrease and the predetermined time period in advance of the step of cleaning.

23. The method according to claim 15, wherein the step of converting further includes calibrating the initial transmittance by substantially eliminating instrumental errors that may occur in the step of measuring.

24. The method according to claim 23, wherein in the step of calibrating, the initial transmittance is multiplied by a calibration multiplier to yield the calibrated initial transmittance.

* * * * *